(12) United States Patent
Wei et al.

(10) Patent No.: US 9,783,604 B2
(45) Date of Patent: Oct. 10, 2017

(54) ENGINEERED ANTI-TGF-BETA ANTIBODIES AND ANTIGEN-BINDING FRAGMENTS

(71) Applicant: GENZYME CORPORATION, Cambridge, MA (US)

(72) Inventors: Ronnie Wei, Bridgewater, NJ (US); Aaron Moulin, Ashland, MA (US); Magali Mathieu, Paris (FR); Clark Pan, Bridgewater, NJ (US); Sunghae Park, Bridgewater, NJ (US); Huawei Qiu, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 14/773,950

(22) PCT Filed: Mar. 11, 2014

(86) PCT No.: PCT/US2014/023274
§ 371 (c)(1),
(2) Date: Sep. 9, 2015

(87) PCT Pub. No.: WO2014/164709
PCT Pub. Date: Oct. 9, 2014

(65) Prior Publication Data
US 2016/0017026 A1    Jan. 21, 2016

Related U.S. Application Data

(60) Provisional application No. 61/776,430, filed on Mar. 11, 2013.

(51) Int. Cl.
| | |
|---|---|
| *C07K 16/22* | (2006.01) |
| *A61K 39/395* | (2006.01) |
| *C12N 15/13* | (2006.01) |
| *A61K 39/00* | (2006.01) |

(52) U.S. Cl.
CPC ........ *C07K 16/22* (2013.01); *A61K 2039/505* (2013.01); *C07K 2317/21* (2013.01); *C07K 2317/55* (2013.01); *C07K 2317/567* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,571,714 A | 11/1996 | Dasch et al. | |
| 5,772,998 A | 6/1998 | Dasch et al. | |
| 5,783,185 A | 7/1998 | Dasch et al. | |
| 6,001,969 A | 12/1999 | Lin et al. | |
| 6,008,011 A | 12/1999 | Lin et al. | |
| 6,046,157 A | 4/2000 | Lin et al. | |
| 6,090,383 A | 7/2000 | Dasch et al. | |
| 6,201,108 B1 | 3/2001 | Lin et al. | |
| 6,419,928 B1 | 7/2002 | Dasch et al. | |
| 6,492,497 B1 | 12/2002 | Thompson et al. | |
| 6,906,026 B1 | 6/2005 | Noble et al. | |
| 7,151,169 B2 | 12/2006 | Thompson et al. | |
| 7,713,924 B2 | 5/2010 | Noble et al. | |
| 7,723,486 B2 | 5/2010 | Ledbetter et al. | |
| 7,763,580 B2 | 7/2010 | Noble et al. | |
| 8,383,780 B2 | 2/2013 | Ledbetter et al. | |
| 8,591,901 B2 | 11/2013 | Ledbetter et al. | |
| 8,597,646 B2 | 12/2013 | Dietz et al. | |
| 8,642,034 B2 | 2/2014 | Streisand et al. | |
| 2011/0301331 A1 | 12/2011 | Glaser et al. | |
| 2013/0034549 A1 | 2/2013 | Harper et al. | |
| 2013/0330352 A1 | 12/2013 | Akita et al. | |
| 2014/0199399 A1 | 7/2014 | Streisand et al. | |
| 2015/0044164 A1 | 2/2015 | Kaplan et al. | |
| 2015/0086547 A1 | 3/2015 | Harper et al. | |

FOREIGN PATENT DOCUMENTS

| | | |
|---|---|---|
| EP | 0 610 427 B1 | 4/2003 |
| EP | 1 175 445 B1 | 7/2004 |
| EP | 2 380 585 A1 | 10/2011 |
| EP | 1 263 464 B1 | 10/2012 |
| EP | 2 012 814 B1 | 5/2013 |
| EP | 2 544 541 B1 | 10/2014 |
| WO | WO-93/09228 A1 | 5/1993 |
| WO | WO-97/13844 A1 | 4/1997 |
| WO | WO-00/40227 A2 | 7/2000 |
| WO | WO-00/66631 A1 | 11/2000 |
| WO | WO-01/66140 A1 | 9/2001 |
| WO | WO-03/061587 A2 | 7/2003 |
| WO | WO-2004/098637 A1 | 11/2004 |
| WO | WO-2006/037029 A2 | 4/2006 |
| WO | WO-2006/086469 A2 | 8/2006 |
| WO | WO-2007/050793 A2 | 5/2007 |
| WO | WO-2007/109254 A2 | 9/2007 |
| WO | WO-2007/121233 A1 | 10/2007 |
| WO | WO-2008/060371 A1 | 5/2008 |
| WO | WO-2010/124276 A2 | 10/2010 |
| WO | WO-2011/112609 A1 | 9/2011 |
| WO | WO-2012/030394 A1 | 3/2012 |

OTHER PUBLICATIONS

Boder et al. Directed evolution of antibody fragments with monovalent femtomolar antigen-binding affinity. Proc Natl Acad Sci U S A. Sep. 26, 2000;97(20):10701-5.*

(Continued)

*Primary Examiner* — David Romeo
(74) *Attorney, Agent, or Firm* — Steptoe & Johnson LLP; Z. Ying Li; Dong Chen

(57) ABSTRACT

Antibodies or antigen-binding fragments thereof are engineered to bind Transforming Growth Factor-β (TGFβ). TGFβ-isoform selective antibodies or antigen-binding fragments thereof may selectively bind human TGFβ1, compared to human TGFβ2 and human TGFβ3, or may selectively bind human TGFβ3, compared to human TGFβ1 and human TGFβ2. The design of the antibodies or antigen-binding fragments thereof is facilitated by a co-crystal structure of a recombinant Fab fragment of GC1008 bound to TGFβ2 and by another co-crystal structure of the scFv version of GC1008 bound to TGFβ1.

17 Claims, 7 Drawing Sheets
(3 of 7 Drawing Sheet(s) Filed in Color)

(56) References Cited

OTHER PUBLICATIONS

International Search Report/ Written Opinion dated Oct. 10, 2014 in PCT/US2014/023274 filed Mar. 11, 2014.
Andersen et al., "Recombinant protein expression for the therapeutic applications," Current Opinion in Biotechnology, vol. 13, pp. 117-123, 2002.
Beck et al., "Strategies and challenges for the next generation of therapeutic antibodies," Nature Reviews Immunology, vol. 10, pp. 345-352, 2010.
Bradbury et al., "Beyond natural antibodies: the power of in vitro display technologies," Nature Biotechnology, vol. 29, No. 3, pp. 245-254, 2011.
Danielpour et al., "Immunodetection and Quantitation of the Two Forms of Transforming Growth Factor-Beta (TGF-β1 and TGF β2) Secreted by Cells in Culture," Journal of Cellular Physiology, vol. 138, pp. 79-86, 1989.
Grütter et al., "A cytokine-neutralizing antibody as a structural mimetic of 2 receptor interactions," PNAS, vol. 105, No. 51, pp. 20251-20256, 2008.
Harding et al., "The immunogenicity of humanized and fully human antibodies," mAbs, vol. 2, No. 3, pp. 256-265, 2010.
Holliger et al., "Engineering bispecific antibodies," Current Opinion in Biotechnology, vol. 4, pp. 446-449, 1993.
Oberlin et al., "Engineering Protein Therapeutics: Predictive Performances of a Structure-Based Virtual Affinity Maturation Protocol," Journal of Chemical Information and Modeling, vol. 52, pp. 2204-2214, 2012.
Peters et al., "Engineering an Improved IgG4 Molecule with Reduced Disulfide Bond Heterogeneity and Increased Fab Domain Thermal Stability," Journal of Biological Chemistry, vol. 287, No. 29, pp. 24525-24533, 2012.
Plückthun, Andreas, "Antibody Engineering: Advances from the Use of *Escherichia coli* Expression Systems," Biotechnology, vol. 9, pp. 545-551, 1991.
Wells, James A., "Additivity of Mutational Effects in Proteins," Biochemistry, vol. 29, No. 37, pp. 8509-8517, 1990.
Zhang et al., "Determination of Fab-Hinge Disulfide Connectivity in Structural Isoforms of a Recombinant Human Immunoglobulin G2 Antibody," Analytical Chemistry, vol. 82, No. 3, pp. 1090-1099, 2010.
Yingling, J. M. et al., "Development of TGF-beta signaling inhibitors for cancer therapy," Nature Reviews, vol. 3, No. 12, pp. 1011-1022, 2004.
Extended European Search Report dated Oct. 4, 2016 in European Patent Application No. 14779440.8.

\* cited by examiner

GB1009(scFv)   TGFβ1 homodimer   GC1009(scFv)

VH Domain          TGFβ1

VH Domain          TGFβ3

| | TGFβ1 | TGFβ2 | TGFβ3 |
|---|---|---|---|
| P53I | 4.3 | 1.6 | 1.3 |
| N59R | 2.4 | 1.1 | 1.5 |
| N59Y | 1.3 | 1.1 | 1.5 |
| G101Y | 1.9 | 1.5 | 2.0 |
| V103R | | | |
| L104K | | | |
| L104R | | | |
| L104W | 4.7 | 2.9 | 5.1 |
| A93R(LC) | | | |

| | kd mutant/kd wt | | | KD mutant/KD wt | | |
|---|---|---|---|---|---|---|
| | TGFb1 | TGFb2 | TGFb3 | TGFb1 | TGFb2 | TGFb3 |
| Y27H | 1.5 | 1.4 | 1.4 | 1.2 | 1.3 | 1.1 |
| S30E | 1.2 | 1.4 | 1.1 | 1.5 | 1.6 | 0.8 |
| S30W | 0.7 | 0.4 | 0.3 | 0.7 | 0.4 | 0.3 |
| S31W | 1.7 | 1.4 | 1.6 | 1.3 | 1.3 | 1.3 |
| N32E | 0.6 | 0.8 | 0.7 | 1.0 | 0.8 | 1.0 |
| N32K | 2.7 | 1.4 | 1.8 | 4.0 | 2.6 | 3.7 |
| I52L | 3.0 | 1.4 | 1.6 | 4.1 | 2.4 | 2.6 |
| I54F | 1.3 | 0.7 | 1.2 | 1.3 | 0.6 | 1.2 |
| I54N | 4.9 | 2.4 | 4.3 | 7.0 | 4.5 | 11.1 |
| I54R | 7.6 | 5.2 | 4.8 | 11.0 | 5.3 | 11.4 |
| I54T | 2.1 | 1.3 | 1.7 | 2.1 | 2.1 | 3.2 |
| I54W | 2.0 | 1.2 | 1.7 | 1.7 | 1.4 | 3.1 |
| V55F | 1.2 | 0.9 | 1.2 | 1.0 | 0.6 | 0.8 |
| D56R | 1.0 | 0.8 | 0.7 | 1.0 | 0.6 | 0.5 |
| E74L | 0.8 | 0.6 | 0.1 | 0.9 | 0.7 | 0.3 |
| E74R | 2.0 | 1.0 | 0.7 | 2.1 | 1.3 | 0.8 |
| E74W | 0.8 | 0.3 | 0.3 | 0.9 | 0.5 | 0.6 |

SEQUENCE LISTING

```
<160> NUMBER OF SEQ ID NOS: 11

<210> SEQ ID NO 1
<211> LENGTH: 120
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 2
<211> LENGTH: 108
<212> TYPE: PRT
<213> ORGANISM: Homo sapiens

<400> SEQUENCE: 2

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30
```

```
Tyr Leu Ala Trp Tyr Gln Gln Lys Pro Gly Gln Ala Pro Arg Leu Leu
             35                  40                  45

Ile Tyr Gly Ala Ser Ser Arg Ala Pro Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Asp Ser Pro
                 85                  90                  95

Ile Thr Phe Gly Gln Gly Thr Arg Leu Glu Ile Lys
                100                 105
```

```
<210> SEQ ID NO 3
<211> LENGTH: 105
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro
                100                 105
```

```
<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105
```

```
<210> SEQ ID NO 5
<211> LENGTH: 112
<212> TYPE: PRT
<213> ORGANISM: Homo sapiens
```

```
<400> SEQUENCE: 5

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
50                  55                  60

Tyr Asn Gln His Asn Pro Gly Ala Ser Ala Pro Cys Cys Val Pro
65                  70                  75                  80

Gln Ala Leu Glu Pro Leu Pro Ile Val Tyr Tyr Val Gly Arg Lys Pro
            85                  90                  95

Lys Val Glu Gln Leu Ser Asn Met Ile Val Arg Ser Cys Lys Cys Ser
        100                 105                 110

<210> SEQ ID NO 6
<211> LENGTH: 112
<212> TYPE: PRT
<213> ORGANISM: Homo sapiens

<400> SEQUENCE: 6

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
            85                  90                  95

Lys Ile Glu Gln Leu Ser Asn Met Ile Val Lys Ser Cys Lys Cys Ser
        100                 105                 110

<210> SEQ ID NO 7
<211> LENGTH: 112
<212> TYPE: PRT
<213> ORGANISM: Homo sapiens

<400> SEQUENCE: 7

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
50                  55                  60

Tyr Asn Thr Leu Asn Pro Glu Ala Ser Ala Ser Pro Cys Cys Val Pro
65                  70                  75                  80
```

```
Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110

<210> SEQ ID NO 8
<211> LENGTH: 5
<212> TYPE: PRT
<213> ORGANISM: Homo sapiens

<400> SEQUENCE: 8

Leu Gly Trp Lys Trp
1               5

<210> SEQ ID NO 9
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Lys Tyr Leu Leu Pro Thr Ala Ala Ala Gly Leu Leu Leu Leu Ala Ala
1               5                   10                  15

Gln Pro Ala Met Ala Gln Val Gln Leu Val Gln Ser Gly Ala Glu Val
            20                  25                  30

Lys Lys Pro Gly Ser Ser Val Lys Val Ser Cys Lys Ala Ser Gly Tyr
        35                  40                  45

Thr Phe Ser Ser Asn Val Ile Ser Trp Val Arg Gln Ala Pro Gly Gln
    50                  55                  60

Gly Leu Glu Trp Met Gly Gly Val Ile Pro Ile Val Asp Ile Ala Asn
65                  70                  75                  80

Tyr Ala Gln Arg Phe Lys Gly Arg Val Thr Ile Thr Ala Asp Glu Ser
                85                  90                  95

Thr Ser Thr Thr Tyr Met Glu Leu Ser Ser Leu Arg Ser Glu Asp Thr
            100                 105                 110

Ala Val Tyr Tyr Cys Ala Ser Thr Leu Gly Leu Val Leu Asp Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Ala Leu Glu Thr
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Gln Ser Leu Gly Ser Ser Tyr Leu
            180                 185                 190

Ala Trp Tyr Gln Gln Lys Pro Gly Gln Ala Pro Arg Leu Leu Ile Tyr
        195                 200                 205

Gly Ala Ser Ser Arg Ala Pro Gly Ile Pro Asp Arg Phe Ser Gly Ser
    210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr Ala Asp Ser Pro Ile Thr
                245                 250                 255
```

```
Phe Gly Gln Gly Thr Arg Leu Glu Ile Lys Arg His His His His
            260                 265                 270
His

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5
```

ENGINEERED ANTI-TGF-BETA ANTIBODIES AND ANTIGEN-BINDING FRAGMENTS

CROSS REFERENCE TO RELATED APPLICATIONS

This application is the National Stage of International Application No. PCT/US2014/023274, filed Mar. 11, 2014, and claims the benefit of U.S. Provisional Application No. 61/776,430, filed Mar. 11, 2013.

SEQUENCE LISTING

The instant application contains a Sequence Listing which has been submitted in ASCII format via EFS-Web and is hereby incorporated by reference in its entirety. Said ASCII copy, created on Sep. 21, 2015, is named 209262-0001-0001-00-530580 ST25,txt and is 10,578 bytes in size.

TECHNICAL FIELD

Antibodies or antigen-binding fragments thereof are engineered to bind Transforming Growth Factor-β (TGFβ). Compositions comprising the antibodies or fragments thereof and methods of using the same for treatment of diseases involving TGFβ activity are provided.

BACKGROUND

Many severe diseases are linked to malfunctions of the TGFβ-induced signaling pathway. An increased tissue level of TGFβ is believed to be a factor in the development of idiopathic pulmonary fibrosis and myocardial fibrosis, for example. Furthermore, high local tissue levels of TGFβ can allow the maintenance and progression of some types of cancer cells. The down-regulation of TGFβ signaling therefore can reduce the viability of such tumor cells.

TGFβ isoforms are ~25 kDa homodimeric molecules with a similar structural framework in which two monomers are covalently linked via a disulfide bridge. The mammalian isoforms share a sequence identity of 70-82%, but have non-overlapping activities in vascular development and the regulation of immune cell function. Three TGFβ isoforms are present in humans: TGFβ1, TGFβ2, and TGFβ3 (Swiss Prot accession numbers P01137, P08112, and P10600, respectively). TGFβ1 and TGFβ3 trigger a cellular signaling cascade upon binding to the extracellular domains of two transmembrane receptors, known as TGFβ receptor types I and II. TGFβ2 binding is also thought to involve TGFβ receptor types I and II, as well as TGFβ receptor type III.

Antibody molecules the can bind human TGFβ1, TGFβ2, and TGFβ3 have been generated (e.g., U.S. Pat. No. 7,723, 486 to Genzyme). Grütter et al. (2008) Proc. Nat'Acad. Sci. USA 105(51): 20251-56, for example, disclose GC1008, a human IgG4 monoclonal antibody (MAb) in clinical development for treating malignancy and fibrotic diseases. GC1008 is a "pan-specific" TGFβ neutralizing antibody, because it can neutralize all three human TGFβ isoforms. GC1008 binds to human TGFβ1, TGFβ2, and TGFβ3 with similar affinities. The TGFβ epitope recognized by GC1008 overlaps the TGFβ binding site for TGFβ receptor types I and II, which is believed to underlie the neutralizing ability of GC1008. Grütter et al. disclose the three dimensional structure of a GC1008 Fab fragment in complex with TGFβ3 at a resolution of 3.1 Å. The complex consists of a TGFβ3 homodimer flanked by two GC1008 Fab fragments. See also Proteopedia entry 3eo0, "Structure of the Transforming Growth Factor-Beta Neutralizing Antibody GC-1008," on the Internet at proteopedia.org/wiki/index.php/3eo0 (last modified Oct. 20, 2012); and Proteopedia entry 3eo1, "Structure of the Fab Fragment of GC-1008 in Complex with Transforming Growth Factor-Beta 3," on the Internet at proteopedia.org/wiki/index.php/3eo1 (last modified Oct. 20, 2012).

SUMMARY

TGFβ-binding antibodies or antigen-binding fragments thereof are disclosed. The TGFβ-binding antibodies or antigen-binding fragments thereof may be pan-specific for all TGFβ isoforms (TGFβ1, TGFβ2 and TGFβ3). Such antibodies or antigen-binding fragments thereof may neutralize all TGFβ isoforms. Alternatively or in addition, the TGFβ-binding antibodies or antigen-binding fragments thereof may selectively bind human TGFβ1, compared to human TGFβ2 and human TGFβ3, or which selectively bind human TGFβ3, compared to human TGFβ1 and human TGFβ2. TGFβ isoform-specific antagonists may exhibit fewer potential side effects. The design of the antibodies or antigen-binding fragments thereof is facilitated by a co-crystal structure of a recombinant Fab fragment of the GC1008 monoclonal antibody, GC1008(Fab) herein, bound to TGFβ2 and by another co-crystal structure of the scFv version of GC1008, known as GC1009 or GC1009(scFv) herein, bound to TGFβ1.

An isolated antibody or antigen-binding fragment thereof may comprise a variant of a PET1073G12 variable heavy chain (VH) domain (SEQ ID NO: 1) having TGFβ paratope and non-paratope residues and a PET1073G12 variable light chain (VL) domain (SEQ ID NO: 2) having TGFβ1 paratope and non-paratope residues, wherein the VH domain comprises up to 20 substitutions of paratope residues and up to 20 substitutions of non-paratope residues;

wherein the VL domain comprises up to 20 substitutions of paratope residues and up to 20 substitutions of non-paratope residues; and wherein said antibody or antigen-binding fragment thereof is capable of binding human TGFβ (TGFβ1, TGFβ2 and TGFβ3).

The antibody or antigen-binding fragment thereof may be capable of binding all three isoforms of human TGFβ, including human TGFβ1, human TGFβ2, and human TGFβ3. The antibody or antigen-binding fragment thereof may bind all three isoforms of human TGFβ with an affinity two-fold, 2.4-fold, three-fold, five-fold, ten-fold, or higher than GC1008(Fab) or GC1009(scFv). The antibody or antigen-binding fragment thereof may comprise a substitution of the Y27, S30, S31, N32, I52, I54, V55, D56, N59, E74 and/or G101 residue. Y27 may be substituted with Ala, Asp, Glu, Phe, Gly, His, Ile, Lys, Leu, Met, Asn, Pro, Gln, Arg, Ser, Thr, Val or Trp. S30 may be substituted with Ala, Cys, Asp, Glu, Phe, Gly, His, Ile, Leu, Met, Asn, Pro, Gln, Arg, Thr, Val, Tyr or Trp. S31 may be substituted with Ala, Glu, Gly, His, Lys, Leu, Pro, Gln, Arg, Thr, Val or Trp. N32 may be substituted with Ala, Asp, Glu, Gly, Leu, Met, Pro, Gln, Arg, Ser, Thr, Val, Trpor Tyr. I52 may be substituted with Val. I54 may be substituted with Ala, Phe, His, Leu, Met, Pro, Thr, Val or Trp. V55 may be substituted with Phe or Gly. D56 may be substituted with Cys, Glu, Phe, Gly, His, Ile, Lys, Len, Asn, Gln, Arg, Ser, Tyr or Val. N59 may be substituted with Arg or Tyr. E74 may be substituted with Ala, Cys, Asp, Phe, Gly, His, Leu, Pro, Gln, Arg, Ser, Thr, Trpor, Tyr. G101 may be substituted with Tyr. The VH domain and/or VL domain may comprise up to 19 substitutions of paratope residues. Preferably, the VH domain and/or VL domain may comprise up to substitutions of paratope residues. A paratope substitution may be selected from the substitutions set forth in TABLE 5. The VH domain and/or VL domain may comprise up to 18 substitutions of non-paratope residues. Preferably, the VH domain and/or VL domain may comprise up to 12 substitutions of non-paratope residues.

Alternatively, the antibody or antigen-binding fragment thereof may be capable of selectively binding human TGFβ1, compared to human TGFβ2 and human TGFβ3. The antibody or antigen-binding fragment thereof may selectively bind TGFβ1 with an affinity two-fold, 2.4-fold, three-fold, five-fold, ten-fold, or higher than GC1008(Fab) or GC1009(scFv). The VH domain and/or VL domain may comprise up to 20 substitutions of paratope residues, preferably up to 19 substitutions of paratope residues, and more preferably up to 12 substitutions of paratope residues. A paratope substitution may be selected from the substitutions set forth in TABLE 5. The VH domain and/or VL domain may comprise up to 20 substitutions of non-paratope residues, preferably up to 18 substitutions of non-paratope residues, and more preferably up to 12 substitutions of non-paratope residues.

Alternatively, the antibody or antigen-binding fragment thereof may be capable of selectively binding human TGFβ3, compared to human TGFβ1 and human TGFβ2. The antibody or antigen-binding fragment thereof may selectively bind TGFβ3 with an affinity two-fold, 2.4-fold, three-fold, five-fold, ten-fold, or higher than GC1008(Fab) or GC1009(scFv). The VH domain and/or VL domain may comprise up to 20 substitutions of paratope residues, preferably up to 19 substitutions of paratope residues, and more preferably up to 12 substitutions of paratope residues. A paratope substitution may be selected from the substitutions set forth in TABLE 5. The VH domain and/or VL domain may comprise up to 20 substitutions of non-paratope residues, preferably up to 18 substitutions of non-paratope residues, and more preferably up to 12 substitutions of non-paratope residues.

In any case above, the antibody may be an IgG1, IgG2, or IgG4 antibody, e.g., a variant of the GC1008 monoclonal antibody. The antigen-binding fragment thereof may be an scFv, e.g., a variant of GC1009(scFv), or a di-scFv, for example. Alternatively, the VH domain may further comprise a human heavy chain constant domain, e.g., an IgG1, IgG2, or IgG4 constant domain, and the VL domain may further comprise a human light chain constant domain, e.g., a κ light chain constant domain. The heavy chain constant domain may have the sequence set forth in SEQ ID NO: 3, and the light chain constant domain may have the sequence set forth in SEQ ID NO: 4. The antigen-binding fragment in this embodiment can be a Fab, a Fab', or a F(ab')$_2$, e.g., a variant of GC1008(Fab).

An isolated nucleic acid may comprise a nucleotide sequence encoding an antibody or antigen-binding fragment thereof. The isolated nucleic acid may be a cDNA. A host cell may comprise the isolated nucleic acid. A method of making an antibody or antigen-binding fragment thereof may comprise culturing the host cell under suitable conditions to produce the antibody or antigen-binding fragment thereof. The antibody or antigen-binding fragment thereof produced by this method may be purified.

A composition may comprise one of the aforementioned antibodies or antigen-binding fragments thereof. The composition may be a pharmaceutical composition. The pharmaceutical composition may comprise a therapeutically effective amount of an antibody or antigen-binding fragment thereof. The composition further may comprise one or more biologically active components.

A method of treating a disease or condition resulting directly or indirectly from TGFβ activity in a human may comprise administering a pharmaceutical composition comprising a therapeutically effective amount of an antibody or antigen-binding fragment thereof. The disease or condition may be selected from the groupconsisting of a fibrotic disease, cancer, or an immune-mediated disease. An antibody or antigen-binding fragment thereof may be used in the manufacture of a medicament for treatment of a disease or disorder selected from the groupconsisting of fibrotic disease, cancer, or an immune-mediated disease. The treatment of the disease or disorder may comprise neutralizing TGFβ1, TGFβ2, and/or TGFβ3. The treatment of the disease or disorder may comprise inhibiting TGFβ1, TGFβ2, and/or TGFβ3 signaling. The treatment of the disease or disorder may comprise inhibiting TGFβ1-, TGFβ2-, and/or TGFβ3-mediated fibronectin production, vascular endothelial growth factor (VEGF) production, epithelial cell proliferation, endothelial cell proliferation, smooth muscle cell proliferation, or immunosuppression. The treatment of the disease or disorder may comprise increasing natural killer cell activity.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 6A and 6B are tables showing the $k_d^{var}/k_d^{wt}$ values of the indicated variant antibodies with regard to their binding affinities for TGFβ1, TGFβ2, and TGFβ3. The $k_d^{var}/k_d^{wt}$ values are presented in a heat map with the color scheme of the heat map shown below the table in FIG. 6A. The blank cells shown in white in the table of FIG. 6B indicate that the $k_d^{var}/k_d^{wt}$ values were not available (N/A). var: variant. wt: wild type.

FIG. 6C is a table showing the $k_d^{mutant}/k_d^{wt}$ and KD mutant/KD wt values of the indicated variant antibodies with regard to their binding affinities for TGFβ1, TGFβ2, and TGFβ3. The $k_d^{mutant}/k_d^{wt}$ and KD mutant/KD wt values are presented in a heat map with the color scheme of the heat map shown below the table in FIG. 6A.

DETAILED DESCRIPTION

Figure 1:
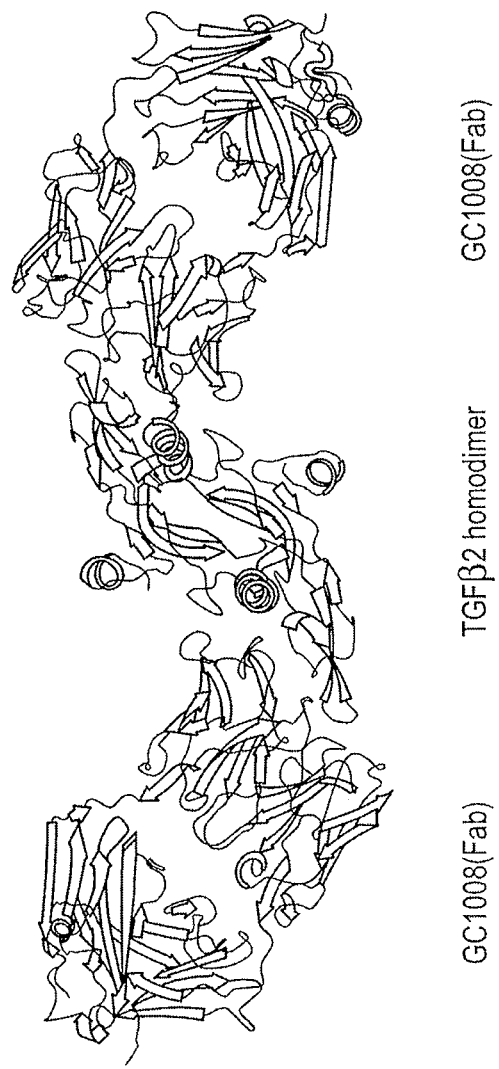
FIG. 1 depicts the co-crystal structure of GC1008(Fab) and human TGFβ2 (SEQ ID NO: 6).

The present TGFβ-binding antibodies or antigen-binding fragments thereof are variants that comprise a modified VH domain of the GC1008 antibody, where the variants comprise an amino acid substitution of the VH and/or VL domain (SEQ ID NO: 1 and SEQ ID NO: 2, respectively). For example, TGFβ antibodies or antigen-binding fragments thereof may comprise a VH domain with an amino acid substitution that confers comparable or improved binding to human TGFβ (TGFβ1, TGFβ2 and TGFβ3) that that observed with the GC1008 antibody. TGFβ-isoform selective antibodies or antigen-binding fragments thereof can bind human TGFβ1 selectively, compared to human TGFβ2 and human TGFβ3, or they can bind human TGFβ3 selectively, compared to human TGFβ1 and human TGFβ2. Selective binding can be achieved by substituting one or more amino acids of the antibodies or antigen-binding fragments thereof comprising a VH domain (SEQ ID NO: 1).

"Selective binding" means that the antibody or antigen-binding fragment thereof (i) can bind a specific isoform of human TGFβ with a higher affinity than an antibody or antigen-binding fragment thereof that comprises an unmodified VH domain of the GC1008 antibody, and/or (ii) can bind the other TGFβ isoforms with a lower affinity than an antibody or antigen-binding fragment thereof that comprises an unmodified VH domain of the GC1008 antibody. For example, an antibody or antigen-binding fragment thereof that selectively binds the TGFβ1 isoform can bind TGFβ1 with a higher affinity than GC1008(Fab) or GC1009(scFv), e.g., two-fold, three-fold, five-fold, ten-fold higher, or more. The antibody or antigen-binding fragment thereof alternatively or in addition can bind TGFβ2 and TGFβ3 with a lower affinity than GC1008(Fab) or GC1009(scFv), e.g., two-fold, three-fold, five-fold, ten-fold lower, or more.

As used herein, a first element "and/or" a second element means a specific disclosure of the first or second element separately, or the first and second elements in combination. The singular forms "a," "an," and "the" include plural referents unless the context clearly dictates otherwise.

Antibodies or Antigen-Binding Fragments Thereof

Antibodies or antigen-binding fragments thereof comprising a modified VH domain of the GC1008 antibody include, but are not limited to, whole antibodies, e.g., IgG, such as IgG1, IgG2, or IgG4, or antigen-binding fragments thereof, e.g., F(ab')$_2$, scFv, Fab, or dAb polypeptides. Monovalent antigen-binding fragments may include Fab, Fv, scFv, and di-scFv, which are two scFv molecules joined by a peptide linker. Antigen-binding fragments may be multivalent, e.g., directed to TGFβ and another antigen. Multivalent fragments include F(ab')$_2$ and di-scFv, where the two scFv components are composed of different variable domains directed to separate antigens. The present antibody or antigen-binding fragment thereof, for example, may be a modified GC1008 (a whole human IgG4 antibody), GC1008(Fab) (a Fab fragment of GC1008), or GC1009(scFv) (an scFv version of GC1008). GC1009(scFv) is a recombinantly produced antigen-binding fragment comprising a human heavy chain PET1073G12 VH domain (SEQ ID NO: 1) and a human light chain PET1073G12 VL domain (SEQ ID NO: 2) linked by a peptide linker, which allows the two domains to associate into an antigen binding site. GC1008 and GC1009 are disclosed in further detail in U.S. Pat. No. 7,723,486 and Grütter (2008). The amino acid sequence of GC1009(scFv) is set forth below, where the peptide linker of the (Gly$_4$/Ser)$_n$ motif (SEQ ID NO: 10) is bolded and italicized and the signal peptide is highlighted in gray:

(SEQ ID NO: 9)
KYLLPTAAAGLLLLAAQPAMAQVQLVQSGAEVKKPGSSVKVSCKASGYTF

SSNVISWVRQAPGQGLEWMGGVIPIVDIANYAQRFKGRVTITADESTSTT

YMELSSLRSEDTAVYYCASTLGLVLDAMDYWGQGTLVTVSS*GGGGSGGGG*

*SGGGG*SALETVLTQSPGTLSLSPGERATLSCRASQSLGSSYLAWYQQKPG

QAPRLLIYGASSRAPGIPDRFSGSGSGTDFTLTISRLEPEDFAVYYCQQY

ADSPITFGQGTRLEIKRHHHHHH.

A "modified" or "variant" variable domain comprises amino acid substitutions, compared to the reference sequence. A "variant VH domain of the GC1008 antibody," for example, may comprise amino acid substitutions compared to the PET1073G12 VH domain with the amino acid sequence set forth in SEQ ID NO: 1.

The VH domain and/or VL domain may comprise up to 20 substitutions of paratope residues, preferably up to 19 substitutions of paratope residues, and more preferably up to 12 substitutions of paratope residues. For example, one of the two domains may comprise a substitution of a paratope residue, while the other domain is unmodified, or both of the domains may comprise paratope residue substitutions. A paratope substitution may be selected from the substitutions set forth in TABLE 5. Paratope substitutions may cause the modified antibody or antigen-binding fragment to bind a TGFβ isoform selectively, or the substitutions may preserve the pan-specific binding of the antibody or antigen-binding fragment to TGFβ isoforms. Both types of paratope substitutions also may be made. For example, a paratope substitution may cause the antibody or antigen-binding fragment to bind a TGFβ isoform selectively, while another paratope substitution that preserves pan-specific binding is made to de-immunize the antibody or antigen-binding fragment. De-immunization can be performed according to the method of Harding et al. (2010) mAbs 2: 256-265, for example.

The VH domain and/or VL domain alternatively or in addition may comprise up to 20 substitutions of non-paratope residues, preferably up to 18 substitutions of non-paratope residues, and more preferably up to 12 substitutions of non-paratope residues. Non-paratope residues may be substituted for various reasons, for example, to increase the thermostability of an antigen-binding fragment, to remove an amino acid residue that is susceptible to oxidation or deamidation, to add an amino acid that can be easily conjugated to a drug or PEG molecules, for example, or to remove a potential carboxylation site.

Modifications can also include amino acid deletions. For example, one or two non-paratope amino acids may be deleted from a variant VH and/or VL domain. The deleted amino acids may be from the carboxyl or amino terminal ends of the VH and/or VL domains.

A variable domain of the present antibodies or antigen-binding fragments thereof comprises three complementarity determining regions (CDRs), each of which is flanked by a framework region (FW). For example, a VH domain may comprise a set of three heavy chain CDRs, HCDR1, HCDR2, and HCDR3. A VL domain may comprise a set of three light chain CDRs, LCDR1, LCDR2, and LCDR3. A set of HCDRs disclosed herein can be provided in a VH domain that is used in combination with a VL domain. A VH domain may be provided with a set of HCDRs as disclosed herein, and if such a VH domain is paired with a VL domain, then the VL domain may be provided with a set of LCDRs disclosed herein. The structures and locations of immunoglobulin variable domain CDR and FW regions are determined herein by reference to Kabat et al. (1987) Sequences of Proteins of Immunological Interest, 4$^{th}$ ed., U.S. Department of Health and Human Services.

The present antibodies or antigen-binding fragments thereof contain "paratope" and "non-paratope" amino acid residues. A "paratope" amino acid of a present antibody or antigen-binding fragment thereof has an atomic nucleus within 4 Å of an atomic nucleus of human TGFβ isoform. Because each human TGFβ isoform forms a structurally different complex with the present antibodies or antigen-binding fragments thereof, the paratope residues may be different for each isoform. A "TGFβ1 paratope residue," for example, has an atomic nucleus within 4 Å of an atomic nucleus of human TGFβ1. TABLE 3 shows paratope residues of the present antibodies or antigen-binding fragments thereof for each of the human TGFβ1, TGFβ2, and TGFβ3 isoforms. A "TGFβ paratope" residue has an atomic nucleus within 4 Å of an atomic nucleus of all three human TGFβ isoforms.

A residue is designated a paratope residue irrespective of location within a CDR or FW region, as defined by the Kabat nomenclature. Many paratope residues are located within CDR regions, as shown in TABLE 4, for example. However, some paratope residues are located within the FW regions. A "non-paratope" amino acid is any amino acid of the antibody or antigen-binding fragment thereof that is not a "paratope" amino acid, irrespective of whether the residue is located in a CDR or FW region.

Antibodies or antigen-binding fragments thereof may comprise heavy chain and light chain amino acid substitutions selected from different human germlines. For example, a set of HCDRs may be introduced into a repertoire of variable domains lacking CDRs using recombinant DNA technology. Germline frameworks include heavy chain sequences from the human DP-10 (V$_H$ 1-69) germline or human DP-88 (V$_H$ 1-e) from the V$_H$-1 family. Light chain sequences may be from the human Vκ3 family, e.g., human DPK-22 (A27). Human germline variable domain amino acid sequences are disclosed by VBASE2 on the Internet at vbase2.org/vbstat.php, for example. For example, a set of HCDRs and a set of LCDRs can be paired together for the PET1073G12, PET1074B9, or PET1287A10 antibodies. The antibody thus can be an IgG4 antibody molecule comprising a modified PET1073G12 VH domain and/or PET1073G12 VL domain, for example. The amino acid sequences of the PET1073G12, PET1074B9, or PET1287A10 domains, including the HCDR and LCDR sets, are disclosed in U.S. Pat. No. 7,723,486.

Antigen-binding fragments may further comprise antibody constant regions or parts thereof. For example, a VL domain may be attached at its C-terminal end to antibody light chain constant domains including human C$_κ$ or C$_λ$ chains. Similarly, an antibody or antigen-binding fragment thereof comprising a VH domain may further comprise attached at its C-terminal end all or part of an immunoglobulin heavy chain (e.g., a CH1 domain) derived from any antibody isotype, e.g., IgG, IgA, IgE, and IgM, or any of the isotype sub-classes, particularly IgG1, IgG2, or IgG4. IgG4 is preferred for some applications because it does not bind complement and does not create effector functions. Where an effector function is desired, IgG1 is preferred. In all cases, the antibody constant regions or parts thereof may be human sequences.

Modifications can be made to the antibody constant regions to improve various properties of the antibodies or antigen-binding fragments thereof. For example, recombinant amino acid modifications can be used to decrease structural homogeneity of the expressed polypeptides. A representative example is Peters et al. (2012) J. Biol. Chem. 287(29): 24525-33, which discloses Cys to Ser substitutions in the IgG4 hinge region that reduce the disulfide bond heterogeneity and increase Fab domain thermal stability. Similarly, Zhang et al. (2010) Anal. Chem. 82: 1090-99 disclose engineering the IgG2 hinge region to limit disulfide bond scrambling and the formation of structural isomers in therapeutic applications. Amino acid modifications to a CH3 domain also can be used to delete carboxy-terminal Lys residues to decrease the number of charge variants. Amino acid modifications also can be used to improve the pharmacological function of recombinant antibodies or antigen-binding fragments thereof. Where antibodies or antigen-binding fragments comprise an Fc region, for example, amino acid modifications can be used to increase complement activation, enhance antibody-dependent cellular cytotoxicity (ADCC) by increasing FcγRIIIA binding or decreasing FcγRIIIB binding, and/or increase serum half-life by increasing FcRn binding. Such amino acid modifications are reviewed in Beck et al. (2010) Nature 10: 345-52, for example.

TABLE 1 below shows the amino acid sequences of the unmodified PET1073G12 VH domain (SEQ ID NO: 1); CH1 domain (SEQ ID NO: 3); PET1073G12 VL domain (SEQ ID NO: 2); and Cκ domain (SEQ ID NO: 4), which are present in GC1008(Fab). The various CDR and framework (FW) regions are labeled; CDR residues also are highlighted.

TABLE 1

VH domain:

| HFW1 | HCDR1 | HFW2 |

QVQLVQSGAEVKKPGSSVKVSCKASGYTFSSNVISWVRQAPGQGLEWMGG

| HCDR2 | HCDR2 | HFW3 |

VIPIVDIANYAQRFKGRVTITADESTSTTYMELSSLRSEDTAVYYCASTL

| HCDR3 | HFW4 |

GLVLDAMDYWGQGTLVTVSS (SEQ ID NO: 1)

CH1 domain:

ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
ESKYGPP
(SEQ ID NO: 3)

VL domain:

| LFW1 | LCDR1 | LFW2 |

ETVLTQSPGTLSLSPGERATLSCRASQSLGSSYLAWYQQKPGQAPRLLIY

| LCDR2 | LFW3 | LCDR3 |

GASSRAPGIPDRFSGSGSGTDFTLTISRLEPEDFAVYYCQQYADSPITFG

LFW4
QGTRLEIK
(SEQ ID NO: 2)

Cκ domain:

RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC
(SEQ ID NO: 4)

Antibodies or antigen-binding fragments thereof may be mono-specific for human TGFβ, or they may be bi-specific. Bi-specific antibodies or antigen-binding fragments thereof can be manufactured in a variety of ways, as disclosed, for example, in Holliger et al. (1993) Current Opinion Biotechnol. 4, 446-449. Examples of bi-specific antibodies include those of dual variable domain IgG (DvD-IgG) technology or the BiTE™ technology, where the binding domains of two antibodies with different specificity can be used and directly linked via short flexible peptides.

Recombinantly Modified VH and/or VL Domains

The heavy chain and/or light chain variable domain of the present antibodies or antigen-binding fragments thereof may be modified recombinantly to alter the amino acid sequence from a germline sequence. For example, one or more of the CDRs in the heavy chain CDR set may be modified, one or more CDRs of the light chain CDR set may be modified, and/or one of the framework regions in the VH and/or VL domains may be modified. Substitutions can be made to paratope amino acids, for example, that strengthen or weaken the binding affinity to a TGFβ isoform, or they can leave the binding affinity relatively unchanged. Other substitutions can be made to non-paratope amino acid residues to confer various characteristics on the antibodies or antigen-binding fragments thereof, e.g., improving stability or introducing a reactive groupof the domain surface that can be covalently modified. Accordingly, the following four categories of amino acid substitutions to the VH and/or VL domain of the present antibodies or antigen-binding fragments thereof are among those contemplated herein: (1) substitutions that confer selective binding to a human TGFβ isoform; (2) substitutions that maintain the pan-specific binding to all three human TGFβ isoforms; (3) substitutions to non-paratope amino acids; and (4) multiple amino acid substitutions. These categories of amino acid substitutions are not mutually exclusive.

1. Substitutions Conferring Selective Binding.

TGFβ-isoform selective antibodies or antigen-binding fragments thereof may comprise an amino acid substitution within the VH domain (SEQ ID NO: 1). For example, the antibodies or antigen-binding fragments thereof can bind human TGFβ1 selectively, compared to human TGFβ2 and human TGFβ3, or can selectively bind human TGFβ3, compared to human TGFβ1 and human TGFβ2. Selective binding can be achieved substituting one or more paratope amino acids.

Figure 2:
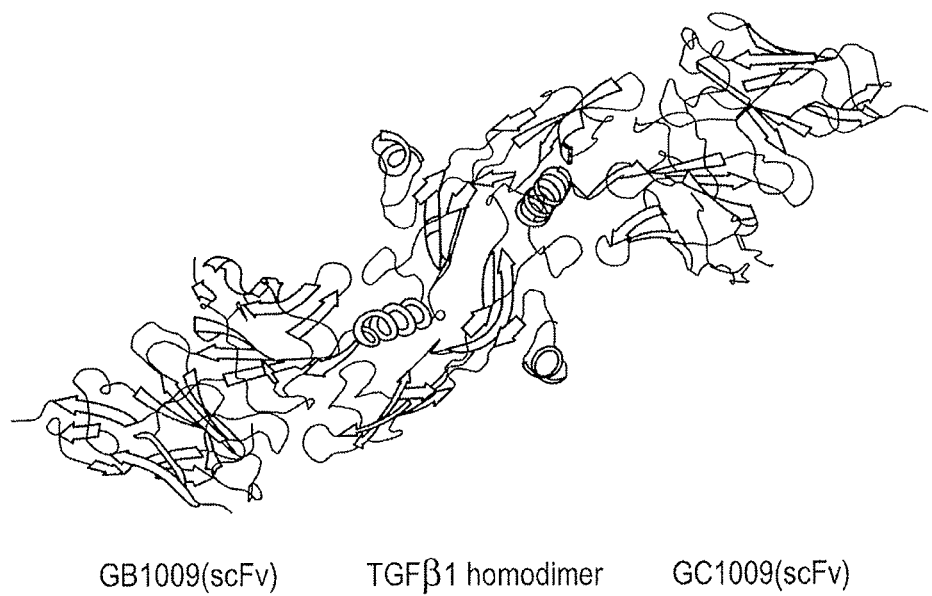
FIG. 2 depicts the co-crystal structure of GC1009(scFv) and human TGFβ1 (SEQ ID NO: 5).
Figure 3:
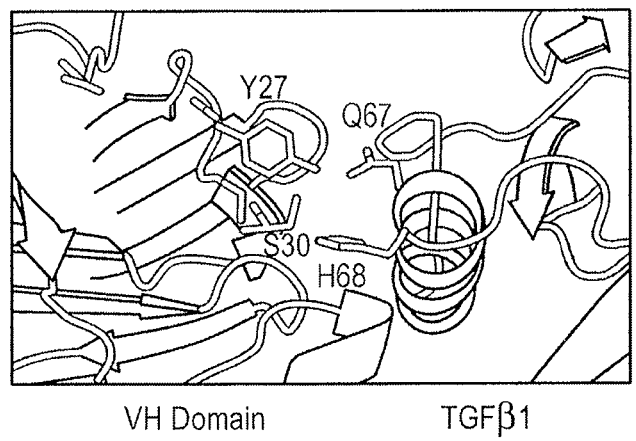
FIG. 3 depicts a portion of the co-crystal structure of GC1009(scFv) VH domain (SEQ ID NO: 1) and human TGFβ1 (SEQ ID NO: 5).
Figure 4:
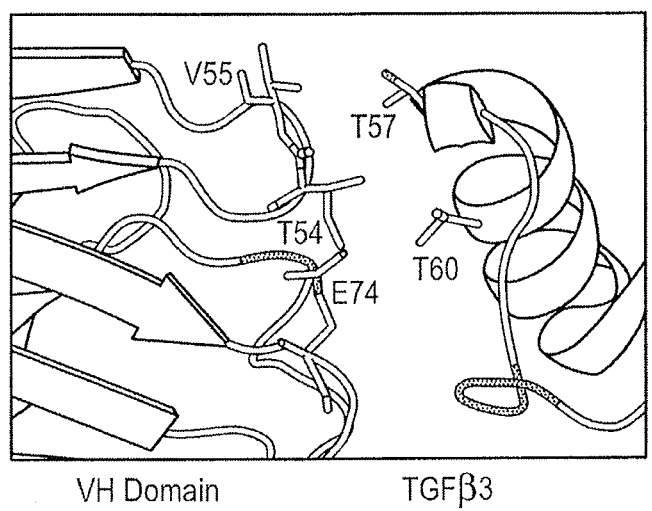
FIG. 4 depicts a portion of the co-crystal structure of GC1008(Fab) VH domain (SEQ ID NO: 1) and human TGFβ3 (SEQ ID NO: 7).

Predicting how an amino acid substitution will affect the ability of an antibody or antigen-binding fragment thereof to interact with a TGFβ isoform is facilitated by a co-crystal structure with each of the TGFβ isoforms. The co-crystal structure of GC1008(Fab) and TGFβ3 is disclosed in Grütter (2008). The co-crystal structure of GC1008(Fab) and TGFβ2 is depicted in FIG. 1. The co-crystal structure of GC1009(scFv) and TGFβ1 is depicted in FIG. 2.

TABLE 2 depicts the amino acid sequence of the human TGFβ1, TGFβ2, and TGFβ3 isoforms. Comparison of co-crystal structures reveals differences in the paratopes between the three isoforms. TGFβ residues in each isoform that interact with GC1008 are bolded in TABLE 2.

TABLE 2

```
            1         10        20        30        40        50        60
TGFβ1   ALDTNYCFSSTEKNCCVRQLYIDFRKDLGWKWIHEPKGYHANFCLGPCPYIWSLDTQYSK
TGFβ2   ALDAAYCFRNVQDNCCLRPLYIDFKRDLGWKWIHEPKGYNANFCAGACPYLWSSDTQHSR
TGFβ3   ALDTNYCFRNLEENCCVRPLYIDFRQDLGWKWVHEPKGYYANFCSGPCPYLRSADTTHST 61        70        80        90       100       112
TGFβ1   VLALYNQHNPGASAAPCCVPQALEPLPIVYYVGRKPKVEQLSNMIVRSCKCS          (SEQ ID NO: 5)
TGFβ2   VLSLYNTINPEASASPCCVSQDLEPLTILYYIGKTPKIEQLSNMIVKSCKCS          (SEQ ID NO: 6)
TGFβ3   VLGLYNTLNPEASASPCCVPQDLEPLTILYYVGRTPKVEQLSNMVVKSCKCS          (SEQ ID NO: 7)
```

TABLE 3 below lists paratope residues of the VH domain (SEQ ID NO: 1) and the VL domain (SEQ ID NO: 2), as determined by the co-crystal structures with each human TGFβ isoform. The GC1008 paratope residues in bold are shared between all three TGFβ isoforms. Three regions of the TGFβ epitope are designated as the "tip," "hydrophobic patch," and "helix three." The VH and VL domain residues having atomic nuclei within 4 Å of an atomic nucleus within the "hydrophobic patch" of TGFβ, which has the sequence $L_{28}GWKW_{32}$ (SEQ ID NO: 8), are conserved for all three isoforms. GC1008 residues interacting with the "tip" and the "helix three" regions, however, show more variability. By comparing all three co-crystal structures, it is evident that GC1008 shifts orientation and adjusts the CDR loop positions and side chain conformations to accommodate all three TGFβ isoforms with similar affinity. See FIG. 1 and FIG. 2. For example, Grütter (2008) disclosed that GC1008 displayed similar affinities for the three isoforms: $IC_{50}$ values of 1±2 nM, 14±5 nM, and 7±2 nM against TGFβ1, TGFβ2, and TGFβ3, respectively in a mink lung epithelial cell (MLEC) proliferation assay. Yet residues 67 and 68 of the three TGFβ isoforms differ in their interactions with the VH paratope residue Y27. The VH residue Y27 makes hydrogen-bonding interactions with TGFβ1 residues Q67 and H68. By contrast, VH residue Y27 forms hydrophobic interactions with T67 and Y50 of TGFβ2 and TGFβ3. This causes a rearrangement of the HCDR1 loop in the TGFβ1 complex, compared to the TGFβ2 and TGFβ3 complexes.

TABLE 3

| Comparison of GC1008 paratopes for TGFβ1/2/3 | TGFβ1 paratope | TGFβ2 paratope | TGFβ3 paratope |
|---|---|---|---|
| TGFβ "Tip" | VH: N59, V103, L104; VL: G30, Y33, A93 | VH: N59, V103, L104; VL: Q27, S28, A93, D94, S95 | VH: L104; VL: Y33, Y92, A93 |

TABLE 3-continued

| Comparison of GC1008 paratopes for TGFβ1/2/3 | TGFβ1 paratope | TGFβ2 paratope | TGFβ3 paratope |
|---|---|---|---|
| TGFβ "Hydrophobic Patch" | VH: S31, N32, I52, I54, V55, I57, N59, L100, G101, L102 | VH: S31, N32, I52, I54, V55, I57, N59, L100, G101, L102 | VH: S31, N32, I52, I54, V55, I57, L100, G101, L102 |
| TGFβ "Helix Three" | VH: Y27, S30, E74 | VH: Y27, S30, D56, E74 | VH: S30, E74 |

The information in TABLE 3 is reformatted in TABLE 4 to indicate the residues of the VH and VL domains that are within 4 Å of an atomic nucleus of TGFβ3 in the co-crystal. Paratope residues are bolded. Most, but not all, of the paratope residues are located within the HCDRs.

TABLE 4

```
            VH sequence (SEQ ID NO: 1)

HFW1                    HCDR1        HFW2
QVQLVQSGAEVKKPGSSVKVSCKASGYTFSSNVISWVRQAPGQGLEWMG
         10         20         30         40

HCDR2  HCDR2                      HFW3
GVIPIVDIANYAQRFKGRVTITADESTSTTYMELSSLRSEDTAVYYCAS
50         60         70         80         90

HCDR3     HFW4
TLGLVLDAMDYWGQGTLVTVSS
100        110        120

VL sequence (SEQ ID NO: 2)

LFW1              LCDR1           LFW2
ETVLTQSPGTLSLSPGERATLSCRASQSLGSSYLAWYQQKPGQAPRLLI
         10         20         30         40

LCDR2           LFW3               LCDR3
YGASSRAPGIPDRFSGSGSGTDFTLTISRLEPEDFAVYYCQQYADSPIT
50         60         70         80         90

LFW4
FGQGTRLEIK
100     108
```

A comparison of co-crystal structures can guide the substitutions to VH and/or VL domain residues to alter the affinity of GC1008 for TGFβ isoforms. In particular, amino acid substitutions can be based on the location of each VH and/or VL residue in the three crystal structures, taking into consideration whether the residue interacts with the antigen or is involved in interactions with other CDRs or structural elements that stabilize the CDR loops. For example, I97 on LCDR3 does not directly interact with TGFβ in any of the three structures; however, I97 faces the interior of the antibody and in a hydrophobic pocket that is also composed of V103 and L104 of the HCDR3. Since V103 and L104 are paratopes important for TGFβ binding, substitution of 197 with medium or small hydrophobic or weakly polar residues could be tolerated without significantly changing the affinity toward TGFβ, e.g., more than ten-fold.

The helix3 region shows the most variability in epitope sequence. Lysine and arginine at position 60 of TGFβ1 and TGFβ2 cause a rotation of GC1008 bound to TGFβ1 and TGFβ2 as compared to TGFβ3. At residues 67 and 68, TGFβ1 has glutamine and histidine, respectively, instead of threonine and isoleucine/leucine as in TGFβ2 and TGFβ3 (FIG. 3). When S30 is mutated to hydrophobic residues such as A, W, additional hydrophobic interactions with conserved TGFβ L64 is favored, and therefore increases the affinity for all three TGFβs. This affinity increase is more pronounced for TGFβ 2 and 3, due to the aforementioned threonine and isoleucine/leucine as in TGFβ2 and TGFβ3 at residues 67 and 68, which favor hydrophobic residues over the Q and H of TGFβ1. In TGFβ1 and TGFβ2, the positively charged side chains at position 60 make ionic interactions with E74 in the heavy chain. Replacement of E74 with positively charged residues is less favored for GC1008 binding to TGFβ1, but more favored to TGFβ3, which has a threonine at position 60 (FIG. 4). Due to the small size of the T60 sidechain of TGFβ3, most mutations can be tolerated at E74 on the heavy chain. Because of the partial hydrophobic nature of T60, hydrophobic substitutions at E74 can also dramatically increase the binding affinity to TGFβ3, often leading to more than two fold of improvement in $k_d^{var}$:$k_d^{wt}$ ratios.

To rapidly select for TGFβ antibodies or antigen-binding fragments thereof with greater affinities to a particular TGFβ isoform or selectivity for one isoform over the other ones, positions listed in Table 3 can be randomized to the other 19 amino acids. This can be achieved by in vitro display of GC1009(scFv), GC1008 Fab fragment, or GC1008 libraries using techniques well known in the art (Bradbury et al. (2011) Nature Biotechnol. 29(3): 245-254). Without the crystal structures of TGFβ1 and TGFβ2 complexed to GC1009 and GC1008 Fab, respectively, antibodies or antigen-binding fragments thereof with higher affinities for only TGFβ3 can be identified using this in vitro display technology based on the TGFβ3-contacting amino acids derived from the TGFβ3 complex structure disclosed in Grütter (2008). With the new TGFβ1 and TGFβ2 complexed to GC1009 and GC1008 Fab structures we have determined, antibodies or antigen-binding fragments thereof with higher affinities for TGFβ1 and TGFβ2 can also be rapidly identified by the display technology. Moreover, having information on all three structures allows one to make more focused libraries to identify isoform selective variants. Focused libraries for TGFβ1 for example would only require randomization of positions 27 and 30 of the VH domain (SEQ ID NO:1). The $32^2$ (1024) possible mutants would be covered by phage libraries with a library size of only ~$10^5$ species. (The 20 amino acids can be represented by 32 codons with a sequence of NNG/C, with any of the four nucleic acids at the first two positions and G or C at the third position.) Without the crystal structures of TGFβ1 and TGFβ2 complexed to GC1009/GC1008, one would have to randomize all 14 TGFβ3-contacting amino acids derived from the TGFβ3 complex structure disclosed in Grütter (2008). A phage library with a diversity of $32^{14}$ ($10^{21}$) would not be fully represented in even the best of any known libraries, which present no more than about ~$10^{11}$ species. Thus, the structure data provided herein would allow the rapid screening and identification of TGFβ selective antagonists.

2. Substitutions Maintaining Pan-Specific Binding.

Substitutions can be made that do not significantly alter the binding affinity toward a TGFβ isoform. A substitution that does not "significantly alter" the binding affinity toward a TGFβ isoform does not increase the ratio of the off-rate of the variant ($k_d^{var}$) compared to the off-rate of the wild-type ($k_d^{wt}$) by more than 2.4 (i.e., $k_d^{var}/k_d^{wt}$ is less than or equal to 2.4). Antibodies or antigen-binding fragments thereof that display "pan-specific binding" for this purpose can have an apparent binding constant for TGFβ (TGFβ1, TGFβ2 and TGFβ3) of at least 10 nM, 30 nM, or 100 nM. Affinity for TGFβ isoforms can be measured using any appropriate technique in the art, for example, the MLEC proliferation assay disclosed in Grütter (2008) or a Biacore® 3000 (GE Healthcare) binding assay. Antibodies or antigen-binding fragments thereof that display "pan-specific binding" for this purpose can have an apparent binding affinity ($k_d^{var}:k_d^{wt}$) for TGFβ (TGFβ1, TGFβ2 and TGFβ3) of less than or equal to 2.4-fold, less than or equal to 3-fold, less than or equal to 5-fold, or less than or equal to 10-fold compared to wild type, preferably less than or equal to 2.4-fold compared to wild type ($k_d^{var}:k_d^{wt}$). These substitutions may be guided by the three co-crystal structures between GC1008/GC1009 and the three TGFβ isoforms. See Oberlin et al. (2012) J. Chem. Inf. Model. 52: 2204-2214.

Substitutions that maintain pan-specific binding to TGFβ are expected to create no steric hindrance with TGFβ amino acid residues or to have a significant detrimental effect on the stability of the antibodies or antigen-binding fragments thereof. Substitutions having a significant detrimental effect on stability can promote aggregation and inactivation of the antibodies or antigen-binding fragments thereof by causing local unfolding or misfolding. The destabilized, aggregated antibodies or antigen-binding fragments thereof can induce immunogenicity, because the patient's immune system can recognize such aggregates as foreign molecules.

An example of a substitution maintaining pan-specific binding is R24 on LCDR1. R24 is oriented away from the TGFβ binding site and is exposed on the VL domain surface. This position can accommodate a substitution with most polar residues except Pro and Cys, which are generally avoided. On the other hand, I52 on HCDR2 makes a close hydrophobic interaction with the "hydrophobic patch" on TGFβ ($L_{28}GWKW_{32}$ (SEQ ID NO: 8)), so I52 substitutions are restricted to medium size hydrophobic residues, with the possibility of a Val substitution, whereas a substitution with a larger hydrophobic residues could create steric hindrance in the bound complex.

TABLE 5 provides non-limiting, examples of amino acid substitutions of the VL domain of SEQ ID NO: 2 (TABLE 5A) and the VH domain of SEQ ID NO: 1 (TABLE 5B). In some cases amino acid substitutions may be made to framework residues within the paratope, e.g., VL residue Y50 in the FW2 region. Antibodies or antigen-binding fragments with one or more of the substitutions below are expected to have a similar pan-specificity and improved affinity toward TGFβ as GC1008/GC1009, i.e., to bind all TGFβ isoforms with isoforms with a binding affinity ($k_d^{var}:k_d^{wt}$) of less than or equal to 2.4-fold, less than or equal to 3-fold, less than or equal to 5-fold, or less than or equal to 10-fold compared to wild type.

TABLE 5A

| | LCDR1 | | LFW2/LCDR2 | | LCDR3 |
|---|---|---|---|---|---|
| R24 | K, N, Q, H, S, T, Y, A, D, E, G, I, L, M, F, P, W, V | Y50 | A, F, W, V, R, N, D, Q, E, G, H, I, L, K, M, P, S, T | Q90 | N, A, R, D, E, G, H, I, L, K, M, F, P, S, T, W, Y, V |
| A25 | G, V, R, N, D, Q, E, H, I, L, K, M, F, P, S, T, W, Y | G51 | A, R, N, D, Q, E, K, S, T, H, I, L, M, F, P, W, Y, V | Q91 | A, R, N, D, E, G, H, I, L, K, M, F, P, S, T, W, Y, V |
| S26 | A, R, N, Q, G, K, M, T, D, E, H, I, L, F, P, W, Y, V | A52 | G, S, R, N, D, Q, E, H, I, L, K, M, F, P, T, W, Y, V | Y92 | S, F, N, A, R, D, Q, E, G, H, I, L, K, M, P, T, W, V |
| Q27 | N, A, D, E, G, H, I, L, M, F, P, S, T, W, Y, V | S53 | A, R, D, N, Q, E, G, K, T, H, I, L, M, F, P, W, Y, V | A93 | G, S, N, D, F, T, Y, V |
| S28 | A, N, G, T, D, Q, E, H, I, L, M, F, P, W, Y, V | S54 | A, N, D, Q, E, G, H, K, Y, R, I, L, M, F, P, T, W, V | D94 | A, N, Q, E, S, T, H, G, I, L, M, F, P, W, Y, V |
| L29 | A, V, R, N, D, Q, E, G, H, I, K, M, F, P, S, T, W, Y | R55 | A, N, K, Q, G, S, T, D, E, H, I, L, M, F, P, W, Y, V | S95 | A, H, N, D, Q, E, G, I, L, M, F, P, T, W, Y, V |
| G30 | A, N, D, Q, E, H, I, L, M, F, P, S, T, W, Y, V | A56 | G, S, R, N, D, Q, E, H, I, L, K, M, F, P, T, W, Y, V | P96 | A, R, N, D, Q, E, G, H, I, L, K, M, F, S, T, W, Y, V |
| S31 | A, N, Q, G, T, R, D, E, H, I, L, K, M, F, P, W, Y, V | | | I97 | L, V, A, G, S, T |
| S32 | A, N, Q, G, T, R, D, E, H, I, L, K, M, F, P, W, Y, V | | | T98 | A, N, G, S, R, D, Q, E, H, I, L, K, M, F, P, W, Y, V |
| Y33 | D, N, E, Q, A, G, H, I, L, M, F, P, S, T, W, V | | | | |
| L34 | V, A, I, R, N, D, Q, E, G, H, K, M, F, P, S, T, W, Y | | | | |

TABLE 5B

| | HFW1/HCDR1 | | HCDR2/HFW3 | | HCDR3 |
|---|---|---|---|---|---|
| G26 | A, S, R, N, D, Q, E, H, I, L, K, M, F, P, T, W, Y, V | G50 | A, R, N, D, Q, E, H, I, L, K, M, F, P, S, T, W, Y, V | T99 | S, A, R, N, D, Q, E, G, H, I, L, K, M, F, P, W, Y, V |

TABLE 5B-continued

| HFW1/HCDR1 | | HCDR2/HFW3 | | HCDR3 | |
|---|---|---|---|---|---|
| Y27 | A, R, N, D, Q, E, G, H, I, L, K, M, F, P, S, T, W, V | V51 | A, G, I, S, T, R, N, D, Q, E, H, L, K, M, F, P, W, Y | L100 | A, I, V, M, F, W, Y, R, N, D, Q, E, G, H, K, P, S, T |
| T28 | A, S, R, N, D, Q, E, G, H, I, L, K, M, F, P, W, Y, V | I52 | V | G101 | A, N, D, Q, E, H, I, L, M, F, P, S, T, W, Y, V |
| F29 | A, S, R, N, D, Q, E, G, H, I, L, K, M, P, T, W, Y, V | P53 | A, G, V | L102 | A, N, Q, M, V, R, D, E, G, H, I, K, F, P, S, T, W, Y |
| S30 | A, R, N, D, Q, E, G, H, I, L, M, F, P, T, W, Y, V, C | I54 | L, A, F, H, M, P, T, V, W | V103 | A, I, L |
| S31 | N, Q, T, A, R, D, E, G, H, I, L, K, M, F, P, W, Y, V | V55 | F, G, H | L104 | A, I, V |
| N32 | D, Q, A, R, E, G, H, I, L, M, F, P, S, T, W, Y, V | D56 | A, N, Q, E, S, T, R, G, H, I, L, K, M, F, V, C | D105 | A, R, N, Q, E, G, H, I, L, K, M, F, P, S, T, W, Y, V |
| V33 | A, R, N, D, Q, E, G, H, I, L, K, M, F, P, S, T, W, Y | I57 | V, L, A, M | A106 | S, R, N, D, Q, E, G, H, I, L, K, M, F, P, T, W, Y, V |
| I34 | V, A, R, N, D, Q, E, G, H, L, K, M, F, P, S, T, W, Y | A58 | G, S, R, N, D, Q, E, H, I, L, K, M, F, P, T, W, Y, V | M107 | L, I, A, R, N, D, Q, E, G, H, K, F, P, S, T, W, Y, V |
| S35 | T, A, R, N, D, Q, E, G, H, I, L, K, M, F, P, W, Y, V | N59 | D, Q, E, Y, A, K, R, G, H, I, L, M, F, P, S, T, W, V | D108 | N, Q, E, G, H, S, T, Y, A, R, I, L, K, M, F, P, W, Y |
| | | Y60 | A, N, Q, H, S, W, R, D, E, G, I, L, K, M, F, P, T, V | Y109 | N, V, I, M, F, A, R, D, Q, E, G, H, L, K, P, S, T, W |
| | | A61 | G, S, R, N, D, Q, E, H, I, L, K, M, F, P, T, W, Y, V | | |
| | | Q62 | A, N, G, H, S, T, Y, R, D, E, I, L, K, M, F, P, W, V | | |
| | | R63 | K, A, N, D, Q, E, G, H, I, L, M, F, P, S, T, W, Y, V | | |
| | | F64 | A, V, R, N, D, Q, E, G, H, I, L, K, M, P, S, T, W, Y | | |
| | | E74 | D, A, R, N, Q, G, H, I, L, K, M, F, P, S, T, W, Y, V, C | | |

3. Substitutions of Non-Paratope Amino Acid Residues.

Non-paratope amino acids can be substituted recombinantly to make a variable light or heavy domain with similar or altered properties compared to the germline variable domain. "Modified" variable domains also include amino acid deletions, as well as substitutions. For example, the N-terminal or C-terminal amino acid residue may be deleted in a modified variable domain.

Non-paratope amino acid substitutions can be made, for example, to increase the stability and/or decrease the tendency to aggregate. Poor stability can affect the ability of an antigen-binding fragment, for example, to fold properly when recombinantly expressed, resulting in a fraction of the expressed fragments being non-functional. Low stability antibodies or antigen-binding fragments thereof also may be prone to forming potentially immunogenic aggregates or may have impaired avidity or shelf-life. scFv polypeptides in particular may demonstrate problems with stability, solubility, expression, aggregation, breakdown products, and overall manufacturability in both bacterial and mammalian expression systems. Framework amino acid substitutions that are expected to increase the stability and/or decrease the tendency to aggregate of a VH and/or VL domain, e.g., in an scFv polypeptide, are disclosed in WO 2007/109254, for example. Substitutions in corresponding residues in the present VH and VL domains are expected similarly to increase stability and/or decrease the tendency to aggregate.

Substitutions that can be tolerated are expected to include those that would replace a non-paratope amino acid of SEQ ID NO: 1 or 2 with a corresponding amino acid that occurs in another human VH or VL domain germline sequence. At present, about 40 variable heavy germline sequences are known in the art, as are about 40 variable kappa germline sequences and about 30 variable lambda germline sequences. A substitution of a non-paratope amino acid with an amino acid occurring in any of these germline sequences is expected to be tolerated. For example, a residue of a VH domain of SEQ ID NO: 1 could be substituted with an amino acid appearing in a corresponding position in any VH germline sequence, e.g., the germline sequence from DP-10 ($V_H$ 1-69) or DP-88 ($V_H$ 1-e). Corresponding positions in this case are determined by a sequence alignment between the various germline sequences, using alignment techniques well known in the art, e.g., ClustalW.

Additional substitutions that are expected to be tolerated are those made to an amino acid with most of its side chain exposed to the solvent, as determined by analysis of the three co-crystal structures. The solvent-accessible surface area of a residue may be estimated using techniques well known in the art. Further, it is expected that substitutions to amino acids buried within the variable domains will be better tolerated if the side chain of the amino acid does not create steric hindrance with adjoining residues. For this reason, buried amino acids generally are substituted with amino acids with side chains of similar or smaller size. For example, a substitution of a buried Ile residue with a Leu, Val, Ala, or Gly is expected to be tolerated. Possible steric hindrance created by a substitution can be predicted by analysis of the three co-crystal structures. Further substitutions that are expected to be tolerated are those maintaining existing electrostatic interactions within the variable domains, e.g., dipole-dipole interactions, induced dipole interactions, hydrogen bonds, or ionic bonds.

Additional amino acid substitutions of variable domains include those expected to confer new useful properties to the antibodies or antigen-binding fragments thereof. For example, putative N-glycosylation sites in the VH and/or VL domains can be removed to prevent or reduce the formation of N-glycoforms. The amino-terminal residue can be substituted with a Gln residue to cause pyroglutamylation, which can decrease the number of charge variants. Amino acid substitutions can be used to lower the isoelectric point, which can decrease the rate of elimination of IgG polypeptide antibodies, for example.

Surface residues of variable domains can be substituted with Cys or Lys residues, for example, which then can be covalently modified and coupled to molecules conferring useful characteristics to the antibodies or antigen-binding fragments thereof, e.g., a detectable label, toxin, targeting moiety, or protein. For example, Cys residue can be coupled to a cytotoxic drug to form a drug conjugate. Cys residues also can be coupled to molecules that increase the serum half-life, e.g., polyethylene glycol (PEG) or serum albumin. Such amino acid modifications are reviewed in Beck et al. (2010) Nature 10: 345-52, for example.

Detectable labels include radiolabels such as $^{131}I$ or $^{99}Tc$, which may be attached to antibodies or antigen-binding fragments thereof using methods known in the art. Labels also include enzyme labels such as horseradish peroxidase. Labels further include chemical moieties such as biotin which may be detected via binding to a specific cognate detectable moiety, e.g., labeled avidin. Other moieties can be attached that facilitate purification. For example, antibodies or antigen-binding fragments thereof can be His-tagged using well-known methods of recombinant modification and expression.

4. Multiple Amino Acid Substitutions to Variable Domains

Multiple amino acid substitutions can be made to the antibodies or antigen-binding fragments thereof. As a general rule, the antibodies or antigen-binding fragments thereof are expected to maintain stability and functionality after at least several randomly selected amino acid substitutions. See, e.g., Wells, Biochemistry 29: 8509-17 (1990). However, as more substitutions are randomly introduced into a variable domain, for example, the overall stability of the domain may decrease, its tendency to aggregate may increase, its affinity for TGFβ may decrease, and its possible immunogenicity may increase. Thus, when multiple amino acid substitutions are made, preferred substitutions are selected from those described above, which are expected to maintain stability and functionality. The functionality of the modified variable domains can be tested using routine methods known in the art, including but not limited to the MLEC proliferation assay disclosed in Grütter (2008).

Nucleic Acids and Methods of Making Antibodies and Antigen-Binding Fragments

A further aspect of the present invention provides nucleic acids encoding antibodies or antigen-binding fragments thereof disclosed herein. The isolated nucleic acid may be a synthetic DNA, a non-naturally occurring mRNA, or a cDNA, for example. The nucleic acid may be inserted within a plasmid, vector, or transcription or expression cassette. A recombinant host cell may comprise one or more constructs above. An "isolated" nucleic acid (or antibody or antigen-binding fragment thereof) is removed from its natural environment, and may additionally be in substantially pure, e.g., at least 90% pure, or in homogeneous form.

Methods of preparing antibodies or antigen-binding fragments thereof comprise expressing the encoding nucleic acid in a host cell under conditions to produce the antibodies or antigen-binding fragments thereof, and recovering the antibodies or antigen-binding fragments thereof. The process of recovering the antibodies or antigen-binding fragments thereof may comprise isolation and/or purification of the antibodies or antigen-binding fragments thereof. The method of production may comprise formulating the antibodies or antigen-binding fragments thereof into a composition including at least one additional component, such as a pharmaceutically acceptable excipient.

Suitable vectors comprising a nucleic acid encoding antibodies or antigen-binding fragments thereof can be chosen or constructed, containing appropriate regulatory sequences, including promoter sequences, terminator sequences, polyadenylation sequences, enhancer sequences, marker genes and other sequences as appropriate. Vectors may be plasmids, phage, phagemids, adenoviral, AAV, lentiviral, for example. Techniques and protocols for manipulation of nucleic acid, for example in preparation of nucleic acid constructs, mutagenesis, sequencing, introduction of DNA into cells, and gene expression, are well known in the art.

Introducing such nucleic acids into a host cell can be accomplished using techniques well known in the art. For eukaryotic cells, suitable techniques may include calcium phosphate transfection, DEAE-Dextran, electroporation, liposome-mediated transfection, and transduction using retroviruses or other viruses, for example. For bacterial cells, suitable techniques may include calcium chloride transformation, electroporation, and transfection using bacteriophage. The introduction may be followed by causing or allowing expression from the nucleic acid, e.g. by culturing host cells under conditions for expression of the gene. In one embodiment, the nucleic acid of the invention is integrated into the genome, e.g., chromosome, of the host cell. Integration may be promoted by inclusion of sequences which promote recombination with the genome, in accordance with standard techniques.

Systems for cloning and expression of a polypeptide in a variety of different host cells are well known. Suitable host cells include bacteria, mammalian cells, plant cells, insect cells, fungi, yeast and transgenic plants and animals. Mammalian cell lines available in the art for expression of a heterologous polypeptide include Chinese hamster ovary (CHO) cells, HeLa cells, baby hamster kidney cells, mouse melanoma cells, rat myeloma cells, human embryonic kidney cells, human embryonic retina cells, and many others. The expression of antibodies and antibody fragments in prokaryotic cells, such as *E. coli*, is well established in the art. For a review, see for example, Plückthun Bio/Technology 9: 545-551 (1991). Expression in cultured eukaryotic cells is also available to those skilled in the art, as reviewed in Andersen et al. (2002) Curr. Opin. Biotechnol. 13: 117-23, for example.

Antibodies or antigen-binding fragments thereof may be glycosylated, either naturally or the choice of expression host, e.g., CHO or NSO (ECACC 85110503) cells, or they may be unglycosylated, for example if produced by expression in a prokaryotic cell. Glycosylation may also be intentionally altered, for example by inhibiting fucosylation, in order to increase ADCC activity of the resulting antibody.

Methods of Using Antibodies or Antigen-Binding Fragments Thereof

The present antibodies or antigen-binding fragments thereof may be used in a method of treatment or diagnosis of the human or animal body, such as a method of treatment (which may include prophylactic treatment) of a disease or disorder in a human patient, which comprises administering an effective amount to the patient. Treatable conditions include any in which TGFβ plays a role, e.g., fibrotic disease, cancer, an immune-mediated disease, and wound healing.

The present antibodies or antigen-binding fragments thereof are useful to treat a disease and condition resulting directly or indirectly from TGFβ activity. The present antibodies or antigen-binding fragments thereof may selectively inhibit the activity of a human TGFβ isoform in vitro or in vivo. Activities of TGFβ isoforms include, but are not limited to, TGFβ-mediated signaling, extracellular matrix (ECM) deposition, inhibiting epithelial and endothelial cell proliferation, promoting smooth muscle proliferation, inducing Type III collagen expression, inducing TGF-β, fibronectin, VEGF, and IL-11 expression, binding Latency Associated Peptide, tumor-induced immunosuppression, promotion of angiogenesis, activating myofibroblasts, promotion of metastasis, and inhibition of NK cell activity. For example, the present antibodies or antigen-binding fragments thereof are useful to treat focal segmental glomerulosclerosis (FSGS), hepatic fibrosis (HF), acute myocardial infarction (AMI), idiopathic pulmonary fibrosis (IPF), scleroderma (SSc), and Marfan Syndrome.

The antibodies or antigen-binding fragments thereof are useful to treat diseases and conditions including, but not limited to, fibrotic diseases (such as glomerulonephritis, neural scarring, dermal scarring, pulmonary fibrosis, lung fibrosis, radiation induced fibrosis, hepatic fibrosis, myelofibrosis), burns, immune mediated diseases, inflammatory diseases (including rheumatoid arthritis), transplant rejection, cancer, Dupuytren's contracture, and gastric ulcers. They are also useful for treating, preventing and reducing the risk of occurrence of renal insufficiencies including but not limited to: diabetic (type I and type II) nephropathy, radiation-induced nephropathy, obstructive nephropathy, diffuse systemic sclerosis, pulmonary fibrosis, allograft rejection, hereditary renal disease (e.g., polycystic kidney disease, medullary sponge kidney, horseshoe kidney), glomerulonephritis, nephrosclerosis, nephrocalcinosis, systemic lupus erythematosus, Sjogren's syndrome, Berger's disease, systemic or glomerular hypertension, tubulointerstitial nephropathy, renal tubular acidosis, renal tuberculosis, and renal infarction. In particular, they are useful when combined with antagonists of the renin-angiotensin-aldosterone system including, but not limited to: renin inhibitors, angiotensin-converting enzyme (ACE) inhibitors, Ang II receptor antagonists (also known as "Ang II receptor blockers"), and aldosterone antagonists. Methods for using antibodies or antigen-binding fragments thereof in combination with such antagonists are set forth in WO 2004/098637, for example.

The antibodies or antigen-binding fragments thereof also are useful to treat diseases and conditions associated with the deposition of ECM, including, systemic sclerosis, post-operative adhesions, keloid and hypertrophic scarring, proliferative vitreoretinopathy, glaucoma drainage surgery, corneal injury, cataract, Peyronie's disease, adult respiratory distress syndrome, cirrhosis of the liver, post myocardial infarction scarring, post angioplasty restenosis, scarring after subarachnoid hemorrhage, multiple sclerosis, fibrosis after laminectomy, fibrosis after tendon and other repairs, scarring due to tattoo removal, biliary cirrhosis (including sclerosing cholangitis), pericarditis, pleurisy, tracheostomy, penetrating central nervous system injury, eosinophilic myalgic syndrome, vascular restenosis, veno-occlusive disease, pancreatitis and psoriatic arthropathy.

The antibodies or antigen-binding fragments thereof further are useful to promote re-epithelialization in diseases and conditions such as venous ulcers, ischaemic ulcers (pressure sores), diabetic ulcers, graft sites, graft donor sites, abrasions and burns, diseases of the bronchial epithelium, such as asthma, ARDS, diseases of the intestinal epithelium, such as mucositis associated with cytotoxic treatment, esophageal ulcers (reflux disease), stomach ulcers, small intestinal and large intestinal lesions (inflammatory bowel disease).

The antibodies or antigen-binding fragments thereof also may be used to promote endothelial cell proliferation, for example, in stabilizing atherosclerotic plaques, promoting healing of vascular anastomoses, or to inhibit smooth muscle cell proliferation, such as in arterial disease, restenosis and asthma.

The antibodies or antigen-binding fragments thereof are useful to enhance the immune response to macrophage-mediated infections. They are also useful to reduce immunosuppression caused, for example, by tumors, AIDS, or granulomatous diseases. The antibodies or antigen-binding fragments thereof are useful to treat hyperproliferative diseases, such as cancers including, but not limited to, breast, prostate, ovarian, stomach, renal, pancreatic, colorectal, skin, lung, cervical and bladder cancers, glioma, mesothelioma, as well as various leukemias and sarcomas, such as Kaposi's sarcoma, and are useful to treat or prevent recurrences or metastases of such tumors. Antibodies or antigen-binding fragments thereof also are useful to inhibit cyclosporin-mediated metastases.

In the context of cancer therapy, "treatment" includes any medical intervention resulting in the slowing of tumor growth or reduction in tumor metastases, as well as partial remission of the cancer in order to prolong life expectancy of a patient.

Methods of treatment comprise administering an antibody or antigen-binding fragment thereof or pharmaceutical compositions comprising the antibody or antigen-binding fragment thereof. The antibody or antigen-binding fragment thereof may be used in the manufacture of a medicament for administration. For example, a method of making a medicament or pharmaceutical composition comprises formulating an antibody or antigen-binding fragment thereof with a pharmaceutically acceptable excipient. A composition may be administered alone or in combination with other treatments, either simultaneously or sequentially dependent upon the condition to be treated.

Administration is preferably in a "therapeutically effective amount" sufficient to show benefit to a patient. Such benefit may be at least amelioration of at least one symptom of a particular disease or condition. The actual amount administered, and rate and time-course of administration, will depend on the nature and severity of the disease or condition being treated. Prescription of treatment, e.g., decisions on dosage etc., may be determined based on preclinical and clinical studies the design of which is well within the level of skill in the art.

The precise dose will depend upon a number of factors, including whether the antibody or antigen-binding fragment thereof is for diagnosis or for treatment, the size and location of the area to be treated, the precise nature of the antibody or antigen-binding fragment thereof, e.g., whole antibody, Fab, or scFv fragment, and the nature of any detectable label or other molecule attached to the antibody or antigen-binding fragment thereof. A typical dose of a whole antibody, for example, can be in the range 100 µg to 1 gm for systemic applications, and 1 µg to 1 mg for topical applications. The dose for a single treatment of an adult patient may be adjusted proportionally for children and infants, and also adjusted for other antibody formats in proportion to molecular weight and activity. Treatments may be repeated at daily, twice-weekly, weekly, monthly or other intervals, at the discretion of the physician. Treatment may be periodic, and the period between administrations is about two weeks or more, preferably about three weeks or more, more preferably about four weeks or more, or about once a month.

Dose levels of about 0.1, 0.3, 1, 3, 10, or 15 mg per kg body weight of the patient are expected to be useful and safe. For example, 0.5-5 mg/kg in rat and mouse has been an effective dose in an acute setting. Therefore, for long-term dosing, 0.3-10 mg/kg may be administered to humans, based on an expected half-life of 21 days. Doses may be sufficient for efficacy, while low enough to facilitate optimal administration. For example, a dose of less than 50 mg facilitates subcutaneous administration. Intravenous administration may be used as the route of delivery for severe diseases, where high doses and the long dosing intervals may be required. Subcutaneous injection can increase the potential immune response to a product. Local administration for localized disease can reduce the amount of administered product and increase the concentration at the site of action, which can improve safety.

An antibody or antigen-binding fragment thereof may be administered by injection, for example, subcutaneously, intravenously, intracavity (e.g., after tumor resection), intralesionally, intraperitoneally, or intramuscularly. An antibody or antigen-binding fragment thereof also may be delivered by inhalation or topically (e.g., intraocular, intranasal, rectal, into wounds, on skin), or orally.

Antibodies or antigen-binding fragments thereof will usually be administered in the form of a pharmaceutical composition, which may comprise at least one component in addition to the antibody or antigen-binding fragment thereof. Thus pharmaceutical compositions may comprise a pharmaceutically acceptable excipient, carrier, buffer, stabilizer or other materials well known to those skilled in the art. Such materials should be non-toxic and should not interfere with the efficacy of the active ingredient. Such materials could include, for example, any and all solvents, dispersion media, coatings, antibacterial and antifungal agents, isotonic and absorption delaying agents. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols, such as mannitol, sorbitol, or sodium chloride in the composition. Additional examples of pharmaceutically acceptable substances are wetting agents or auxiliary substances, such as emulsifying agents, preservatives or buffers, which increase the shelf life or effectiveness.

The precise nature of the carrier or other material will depend on the route of administration. For intravenous injection, or injection at the site of affliction, the active ingredient will be in the form of a parenterally acceptable aqueous solution which is pyrogen-free and has suitable pK, isotonicity, and stability. Those of relevant skill in the art are well able to prepare suitable solutions using, for example, isotonic vehicles such as sodium chloride injection, Ringer's injection, and lactated Ringer's injection. Preservatives, stabilizers, buffers, antioxidants and/or other additives may be included.

An antibody or antigen-binding fragment thereof may be formulated in liquid, semi-solid or solid forms such as liquid solutions (e.g., injectable and infusible solutions), dispersions or suspensions, powders, liposomes, and suppositories. The preferred form depends on the intended mode of administration, therapeutic application, the physicochemical properties of the molecule, and the route of delivery. Formulations may include excipients, or combinations of excipients, for example: sugars, amino acids and surfactants. Liquid formulations may include a wide range of antibody concentrations and pH. Solid formulations may be produced by lyophilization, spray drying, or drying by supercritical fluid technology, for example.

Therapeutic compositions can be formulated as a solution, microemulsion, dispersion, liposome, or other ordered structure suitable to high drug concentration. Sterile injectable solutions can be prepared by incorporating the antibody or antigen-binding fragment thereof in an appropriate solvent with one or a combination of ingredients enumerated above, followed by filtered sterilization. Generally, dispersions are prepared by incorporating the active compound into a sterile vehicle that contains a basic dispersion medium and other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by using a coating such as lecithin, by maintaining the particle size of a dispersion, or by using surfactants. Prolonged absorption of injectable compositions can be brought about by including in the composition an agent that delays absorption, for example, monostearate salts and gelatin.

In certain embodiments, the active compound may be prepared with a carrier that will protect the antibody or antigen-binding fragment thereof against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

A method of using an antibody or antigen-binding fragment thereof may comprise causing or allowing binding to TGFβ. Such binding may take place in vivo, e.g., following administration of an antibody or antigen-binding fragment thereof to a patient, or it may take place in vitro, e.g., in ELISA, Western blotting, immunocytochemistry, immunoprecipitation, affinity chromatography, or cell based assays, or in ex vivo based therapeutic methods, e.g., methods in which cells or bodily fluids are contacted ex vivo with an antibody or antigen-binding fragment thereof and then administered to a patient.

A kit comprising an antibody or antigen-binding fragment thereof is provided. The antibody or antigen-binding fragment thereof may be labeled to allow its reactivity in a sample to be determined. Kits may be employed in diagnostic analysis, for example. A kit may contain instructions for use of the components. Ancillary materials to assist in or to enable performing such a method may be included within the kit.

The reactivity of an antibody or antigen-binding fragment thereof in a sample may be determined by any appropriate means, e.g., radioimmunoassay (RIA). Radioactively labeled antigen may be mixed with unlabeled antigen (the test sample) and allowed to bind to the antibody or antigen-binding fragment thereof. Bound antigen is physically separated from unbound antigen and the amount of radioactive antigen bound to the antibody or antigen-binding fragment thereof is determined. A competitive binding assay also may be used with non-radioactive antigen, using an antigen or an analogue linked to a reporter molecule. The reporter molecule may be a fluorochrome, phosphor, or dye. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are colored, magnetic or paramagnetic, and biologically or chemically active agents that can directly or indirectly cause detectable signals to be visually observed, electronically detected or otherwise recorded. These molecules may be enzymes that catalyze reactions that develop or change colors or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. The signals generated by antibody-reporter conjugates may be used to derive quantifiable absolute or relative data of the relevant antibody binding in samples.

The present invention also provides the use of an antibody or antigen-binding fragment thereof for measuring antigen levels in a competition assay. Linking a reporter molecule to the antibody or antigen-binding fragment thereof so that a physical or optical change occurs on binding is one possibility. The reporter molecule may directly or indirectly generate detectable, and preferably measurable, signals. The linkage of reporter molecules may be directly or indirectly, covalently, e.g., via a peptide bond or non-covalently. The antibody or antigen-binding fragment thereof and a protein reporter may be linked by a peptide bond and recombinantly expressed as a fusion protein.

Further aspects and embodiments of the present invention will be apparent to those skilled in the art in the light of the present disclosure, including the following experimental exemplification.

EXAMPLE 1

Anti-TGFβ single chain Fv (scFv) may be prepared according to the following non-limiting example disclosed in Example 1 of U.S. Pat. No. 7,723,486. The neutralization potencies for TGFβ1, TGFβ2, and/or TGFβ3 can be increased using mutagenesis and/or combinatorial techniques. scFv with improved potencies for TGFβ1, TGFβ2, and/or TGFβ3 can be generated by selecting and screening phage antibody libraries as described in Example 1 of U.S. Pat. No. 7,723,486. The scFvs generated in that example were compared to 1D11.16, which is disclosed in U.S. Pat. No. 7,723,486, in the MLEC proliferation assay.

In Example 1 of U.S. Pat. No. 7,723,486, particular germlines were found to be highly represented amongst the population of high potency, TGFβ-neutralizing scFvs. These were DP-10/1-69 and DP-88/1-e (both members of the VH1 germline family) for the heavy chain, and DPK22/A27 ($V_\kappa 3$ family) for the light chain. These germlines appear to provide a structural framework particularly suitable for high potency, TGFβ pan-neutralizing antibodies. PET1073G12, PET1074B9, and PET1287A10 scFvs showed potencies approaching or exceeding those of 1D11.16 on all three TGFβ isoforms in the MLEC proliferation assay.

The derived amino acid sequences of PET1073G12, PET1074B9, and PET1287A10 VH and VL gene segments were aligned to the known human germline sequences in the VBASE database (Tomlinson, V-BASE sequence directory, MRC Centre for Protein Engineering, Cambridge, UK, at hypertext transfer protocol vbase.mrc-cpe.cam.ac.uk (1997)), and the closest human germline was identified by sequence similarity. The closest human germline gene for the VH gene segment of PET1073G12 and PET1074B9 was identified as DP-10/1-69 (VH1 germline family) and the closest human germline gene for the VH gene segment of PET1287A10 was identified as DP-88/1-e (VH1 germline family). The closest human germline gene for the VL gene segment of PET1073G12, PET1074B9, and PET1287A10 was identified as DPK22/A27 ($V_\kappa 3$ germline family). Site-directed mutagenesis was used to substitute framework residues that differed from germline to the germline residue, provided that such changes did not produce a loss of potency in the MLEC proliferation assay of more than three-fold in the resulting antibody on any TGFβ isoform. If such a loss of potency was observed, the non-germline framework amino acid was kept in the final antibody.

In germlined PET1073G12 and germlined PET1074B9, all framework residues are germline except for two residues in VH and one residue in VL. The amino acid sequences for germlined PET1073G12 are described in SEQ ID NO: 2 for VH and SEQ ID NO: 7 for VL of U.S. Pat. No. 7,723,486. The amino acid sequences for germlined PET1074B9 are described in SEQ ID NO: 12 for VH and SEQ ID NO: 17 for VL of U.S. Pat. No. 7,723,486. In germlined PET1287A10, all VH and VL framework residues are germline. The amino acid sequences for germlined PET1287A10 are described in SEQ ID NO: 22 for VH and SEQ ID NO: 27 for VL of U.S. Pat. No. 7,723,486.

EXAMPLE 2A

Neutralization potency of anti-TGFβ antibodies or antigen-binding fragments thereof can be assayed using the TGFβ dependent MLEC proliferation assay disclosed in Example 4 of U.S. Pat. No. 7,723,486. The MLEC proliferation assay is based on an assay described by Danielpour et al., J. Cell. Physiol., 138:79-86 (1989). This assay works on the principle that TGFβ1, TGFβ2, or TGFβ3 added to mink lung epithelial cells inhibits serum induced cell proliferation. Antibodies were tested for neutralization of TGFβ1, TGFβ2, or TGFβ3 resulting in the restoration of the cell proliferation. Proliferation was measured by the uptake of [$^3$H]-thymidine. The potency of the antibody was defined as the concentration of the antibody that neutralized a single concentration of TGFβ1, TGFβ2, or TGFβ3 at a level of 50% ($IC_{50}$) in nM.

MLEC proliferation assay protocol: the MLEC line was obtained from the American Type Culture Collection (Cat.# CCL-64). Cells were grown in Minimum Essential Media (MEM, Gibco) containing 10% fetal bovine serum (FBS) (Gibco), 1% penicillin/streptomycin (Gibco) and 1% MEM non-essential amino acids solution (Gibco). Confluent cells from T-175 flasks were dissociated from the flask, spun down, washed, and resuspended in MLEC assay media that was made of MEM containing 1% FBS, 1% penicillin/streptomycin and 1% MEM non-essential amino acids solution. An aliquot of the cells was then labeled with trypan blue, counted on a haemocytometer, and the cell stock diluted to $1.75 \times 10^5$ cell per ml using assay media. 100 µL of this suspension was added to each well of a tissue culture flat-bottomed 96 well plate and incubated for 3 to 5 hours.

Preparation of TGFβ/antibody solutions: working solutions of TGFβ1, TGFβ2, or TGFβ3 at 6 ng/ml (six times the final assay concentration) and antibodies (including controls such as 1D11.16) at three times the final maximum assay concentration were prepared in MLEC assay media. The final concentration of TGFβ in the assay (1 ng/ml or 40 pM) corresponded to the concentration that induced approximately 80% inhibition of cell proliferation compared to the control with no TGFβ (i.e., $EC_{80}$ value).

Dilution plate set up: samples of test and control antibodies were titrated in 3-fold dilution steps in MLEC assay media and incubated in the presence and absence of TGFβ1, TGFβ2 or TGFβ3. All relevant controls were included in every experiment: testing of the 1D11.16 and/or reference antibody as appropriate and performing TGFβ1, TGFβ2, or TGFβ3 titrations. Completed plates were left in a humidified tissue culture incubator for 1 hour±15 minutes.

Addition of TGFβ/antibody solutions to the plated cells: after the appropriate incubation times, 100 µL from each well of the dilution plates were transferred to the plated MLEC and the plates returned to the incubator for 44±2 hours. 25 µL of 10 µCi/ml [$^3$H]-thymidine diluted in phosphate buffered saline (PBS) was added to each of the wells (0.25 µCi/well). The plates were then returned to the incubator for 4 hours±30 minutes.

Cell harvesting: 100 µL of trypsin-EDTA (0.25%, Gibco) was added to each well, plates were incubated for 10 minutes in the incubator, and cells were harvested using a Tomtec or Packard 96 well cell harvester.

Data accumulation and analysis: data from the harvested cells were read using a beta-plate reader (TopCount, Packard). Data were analyzed to obtain $IC_{50}$ and standard deviation values. $IC_{50}$ values were obtained by using the Prism 2.0 (GraphPad) software.

Results: purified PET1073G12, PET1074B9, and PET1287A10 germlined IgG4s were tested alongside 1D11.16 in the MLEC proliferation assay. IgG4s were produced as described in Example 3 of U.S. Pat. No. 7,723,486. Mean $IC_{50}$ data for PET1073G12 and PET1287A10 IgG4s showed that these antibodies have potencies similar or approaching those of 1D11.16 on TGFβ1, TGFβ2, and TGFβ3.

Mean $IC_{50}$ data suggests that PET1074B9 IgG4 is more potent on TGFβ1, although a full dose response curve was not obtained in the MLEC assay. By comparison, 1D11.16 showed 12% neutralization on TGFβ1 at a concentration of 91 pM, and PET1074B9 showed 78% neutralization at a similar concentration of 92 pM.

Example 2B

Additionally, the TGFβ isoform binding affinity of the GC1008 antibody was measured using a Biacore® 3000 (GE Healthcare) instrument. TGFβ1 and TGFβ2, produced in-house, were diluted to ~1 µg/mL in 10 mM acetate, pH 4.5, and TGFβ3 (R&D Systems) was diluted to ~2 µg/mL in 10 mM acetate, pH 4.0. Flowcells 2, 3, and 4 of a CM5 sensor chip were covalently immobilized with 50 to 100 RU of TGFβ1, TGFβ2, and TGFβ3, respectively, using the standard amine coupling kit from GE Healthcare. Flowcell 1 was used as a control surface. For kinetic binding analysis, GC1008 was serially diluted 1:3 from 33.3 nM to 1.2 nM in HBS-E buffer and injected in triplicate to all four flowcells for 5 min, followed by 5 min dissociation in buffer at a 30 µL/min flow-rate. The surface was regenerated with two 30 sec injections of 40 mM HCl at 75 µL/min. The sensorgrams were fit using a 1:1 binding model after subtraction of buffer and control flowcell refractive index changes with the BIA Evaluation Software Kit (GE Healthcare). The $K_D$'s shown in TABLE 6 are an average of more than 25 independent assays.

TABLE 6

| Isoform | $K_D$ (nM) |
|---|---|
| TGFβ1 | 1.7 ± 0.6 |
| TGFβ2 | 3.0 ± 1.2 |
| TGFβ3 | 2.0 ± 1.2 |

EXAMPLE 3

The biologic efficacy of antibodies or antigen-binding fragments thereof for treating chronic renal disease and other clinical indications can be determined using the rat unilateral ureteral obstruction (UUO) model set forth in Example 7 of U.S. Pat. No. 7,723,486. Adult Sprague Dawley rats (Taconic Farms, Germantown, N.Y.) weighing 250-280 gram (about 6 weeks) were housed in an air-, temperature-, and light-controlled environment. Rats undergoing UUO received a small ventral midline abdominal incision to expose the left kidney and upper ureter. The ureter was ligated at the level of the lower pole of the kidney with silk suture and a second time at about 0.2 cm below the first one. Sham operated rats received the same surgical protocol but without ureteral ligation.

The obstructed rats were treated with PBS, a murine pan-neutralizing monoclonal antibody (1D11), an isotype-matched control antibody (13C4), or a human pan-neutralizing TGF-β monoclonal antibody as disclosed in U.S. Pat. No. 7,723,486. The antibodies were administered to the rats intraperitoneally beginning on the day of ureteral ligation for a course of 3 weeks. 13C4 and 1D11 were administered at 5 mg/kg (3 times/week), and the human pan-neutralizing antibody was given to the rats at 5 mg/kg (every 5 days). At the end of 3 weeks, the rats were sacrificed, the kidneys were perfused with PBS for 3 minutes, and the perfused kidneys were harvested for the analysis of mRNA, determination of collagen content, and histological examination.

To assess the extent of tissue fibrosis, total tissue collagen content was determined by biochemical analysis of hydroxyproline in hydrolyzate extracts according to Kivirikko et al. A Sircol collagen assay was also performed for total collagen content. The Sircol collagen assay measures the amount of total acid/pepsin soluble collagens based on the specific binding of Sirius red dye with the side chain of tissue collagen.

The UUO rats treated with the human pan-neutralizing monoclonal antibody showed a 43.4% reduction in hydroxyproline content (1.98±0.26 µg/mg dry tissue) when compared to the PBS treated group(3.5±0.3 µg/mg dry tissue, p<0.05). The lessening in renal fibrosis was further supported by the reduction in total solubilized collagen in the affected kidneys, as determined by a Sirius red dye based assay (sham: 18.5±2.6, PBS: 69.3±3.8, and human pan-neutralizing monoclonal antibody: 35.6±5.2 µg/100 mg tissue, p<0.05 vs. PBS).

The ability of a human pan-neutralizing anti-TGF-β monoclonal antibody to reduce tissue fibrosis by immunohistochemical examination was also assessed. In control animals, ureteral obstruction for three weeks caused widespread disruption of renal tubular architecture with marked distension, cellular atrophy and necrosis/apoptosis, tissue inflammation and tubulointerstitial expansion with evident fibrosis. There was little evidence of glomerular damage. Rats treated with 1D11 or the human pan-neutralizing monoclonal antibody, on the other hand, showed preservation of renal architecture as judged by attenuated tubular dilation and disorganization, reduced inflammatory infiltrates (cellularity) and diminished tubulointerstitial expansion and fibrosis.

The effect of treatment with a human pan-neutralizing anti-TGF-β monoclonal antibody on TGF-β regulated gene expression was also measured. TGF-β1 mRNA was reduced in the human pan-neutralizing monoclonal antibody-treated UUO animals compared to either PBS-treated or 13C4 control antibody-treated animals. A significant decrease in mRNA levels for type III collagen also was seen in the obstructed kidneys treated with the human and murine anti-TGF-β antibodies as compared to those treated with PBS or 13C4 indicating a decrease in collagen synthesis.

The efficacy of a human pan-neutralizing anti-TGF-β monoclonal antibody to reduce auto-induced TGF-β synthesis was further confirmed by measuring the total renal TGF-β1 protein. Compared to the sham-operated animals, obstructed kidneys exhibited a marked increase in total tissue TGF-β1. Obstructed rats dosed with a human pan-neutralizing monoclonal antibody, however, showed 75% reduction of tissue TGF-β1 levels, below the levels recorded for both control groups. By comparison, the murine 1D11 antibody reduced tissue TGFβ-1 levels by 45%, compared to control groups. The above-described results demonstrate that the TGF-β neutralization with a human pan-neutralizing anti-TGF-β monoclonal antibody interrupted the TGF-β autocrine-regulation loop concomitant with prevention of TGF-β1 production and collagen III mRNA expression.

The effect of a human pan-neutralizing anti-TGF-β monoclonal antibody on the expression of smooth muscle actin (α-SMA) was further determined as an indirect indicator of TGF-β inhibition. Smooth muscle actin expression is an indicator of activated myofibroblasts, which are associated with tissue fibrosis and produce fibrous connective tissue. TGF-β is an inducer of the activation and phenotypic transformation of stromal fibroblasts and resident epithelial cells to myofibroblastic cells. α-SMA protein was detected by standard Western blot analysis.

When compared with sham-operated animals, rats with obstructed kidneys showed dramatic up-regulation in α-SMA protein as measured by western blotting of tissue homogenates. Obstructed kidneys dosed with a human pan-neutralizing anti-TGF-β monoclonal antibody showed significant reduction (75% compared to PBS controls) in measureable α-SMA expression.

These results demonstrate the efficacy of a human pan-neutralizing anti-TGF-β monoclonal antibody in reducing collagen deposition in the fibrotic kidneys, clearly indicating that the antibody is a potent inhibitor of renal collagen production and deposition in this model of severe renal injury and tubulointerstitial fibrosis. Because the process of tissue fibrosis in organs such as in lung, liver or kidney possesses common mechanisms or pathways, the skilled artisan will appreciate that the antibody is useful in the treatment of chronic renal diseases as well as other clinical indications characterized by pathogenic fibrosis.

EXAMPLE 4

The structure of the GC1008(Fab)-TGFβ2 complex was determined as follows. Recombinant GC1008(Fab) with a C-terminal His6 tag (SEQ ID NO: 11) was transiently expressed in HEK293FS cells and purified over Nickel-NTA affinity resin, followed by size exclusion chromatography. The purified GC1008(Fab) was mixed with TGFβ2 homodimer and the complex was isolated using size exclusion chromatograph. The GC1008(Fab)-TGFβ2 complex was crystallized in 35% PEG400, 100 mM 2-(N-morpholino) ethanesulfonic acid (pH 6.0) at 20° C. and further optimized by seeding and pH optimization. The final data set was collected to 2.83 Å in space groupP$2_12_12$, and the structure was solved using molecular replacement with the GC1008 (Fab)-TGFβ3 structure disclosed in Grütter (2008). The structure of the GC1008(Fab)-TGFβ2 complex is depicted in FIG. 1.

EXAMPLE 5

The structure of the GC1009(scFv)-TGFβ1 complex was determined as follows. Recombinant GC1009(scFv) with a C-terminus His6 tag (SEQ ID NO: 11) was overexpressed in *E. coli* and purified over Nickel-NTA affinity resin, followed by size exclusion chromatography. The purified GC1009 (scFv) was mixed with TGFβ1 homodimer, and the complex was isolated using size exclusion chromatograph. The GC1009(scFv)-TGFβ1 complex was crystallized in 16% PEG 4K, 0.1 M citrate (pH 5.0), 4% 2-propanol at 21° C. The structure was determined to 3.00 Å in space groupC2, and the structure was solved using molecular replacement with the GC1008(Fab)-TGFβ2 structure determined in EXAMPLE 4. The structure of the GC1009(scFv)-TGFβ1 complex is depicted in FIG. 2.

EXAMPLE 6

Plasmids encoding either the GC1008 heavy chain or light chain were used as a template in PCR-based mutagenesis reactions. Mutations to the encoding DNA were made to create 155 single amino acid substitutions of the encoded heavy chain amino acid sequence and one single amino acid substitution of the encoded light chain amino acid sequence. A QuikChange® Lightning Site-Directed Mutagenesis kit (Agilent Technologies, Santa Clara Calif.) was used according to the manufacturer's instructions to create DNA mutations using a set of forward and reverse primers, either designed for a specific amino acid or for all 20 amino acids with a degenerate codon (NNK). After sequencing confirmation, identified mutant DNA was paired with a wild-type light or heavy chain DNA for transfection into an Expi293F™ host cell suspension (Life Techonologies Corp., Grand Island, N.Y.). At 4 days post-transfection, conditioned media (1 mL) was harvested and purified using a 1 mL Protein A PhyTip® column (PhyNexus, Inc., San Jose, Calif.) and a PureSpeed™ 12-channel pipette (Rainin Instrument LLC, Oakland, Calif.). Purified variant antibody samples were analyzed in duplicate on a Biacore® 3000 (GE Healthcare) at 50 nM concentrations, using the 100 RU level TGFβ1, 2, and 3 immobilized surfaces. The off-rate ($k_d$) of the variants was divided by the $k_d$ of the wild-type control to obtain the fold change in the $k_d$. An increase in affinity was indicated if $k_d^{var}/k_d^{wt}$) was less than 1, and a reduction was indicated, if the value was larger than 1. A heat map was generated to visualize the results. Variants that completely lost affinity for TGFβ were shown in red without numbers. The results are shown in FIGS. 6A-6C.

In FIG. 6C, seventeen mutants were selected and scaled up to produce sufficient amount of purified protein for KD (equilibrium constant =kd/ka) analysis by Biacore. Multiple concentrations (90, 30, 10 and 3.33 nM) were used in duplicate on the 150 RU level TGFβ1, 2, and 3 immobilized surfaces. KD was calculated using global curve fitting analysis for a 1-to-1 Langmuir binding model. The experimental data from all four concentrations were used for calculation except for I54N and I54R mutants, where only the top 2 concentrations were used. The fold changes in KD were compared to the fold changes in kd (off rate) presented in FIG. 6B, and a heat map was generated for visualization. Similar fold changes were observed from the two data sets, confirming the validity of using kd as a parameter for screening of 155 single mutants as shown in FIG. 6B.

Figure 5:
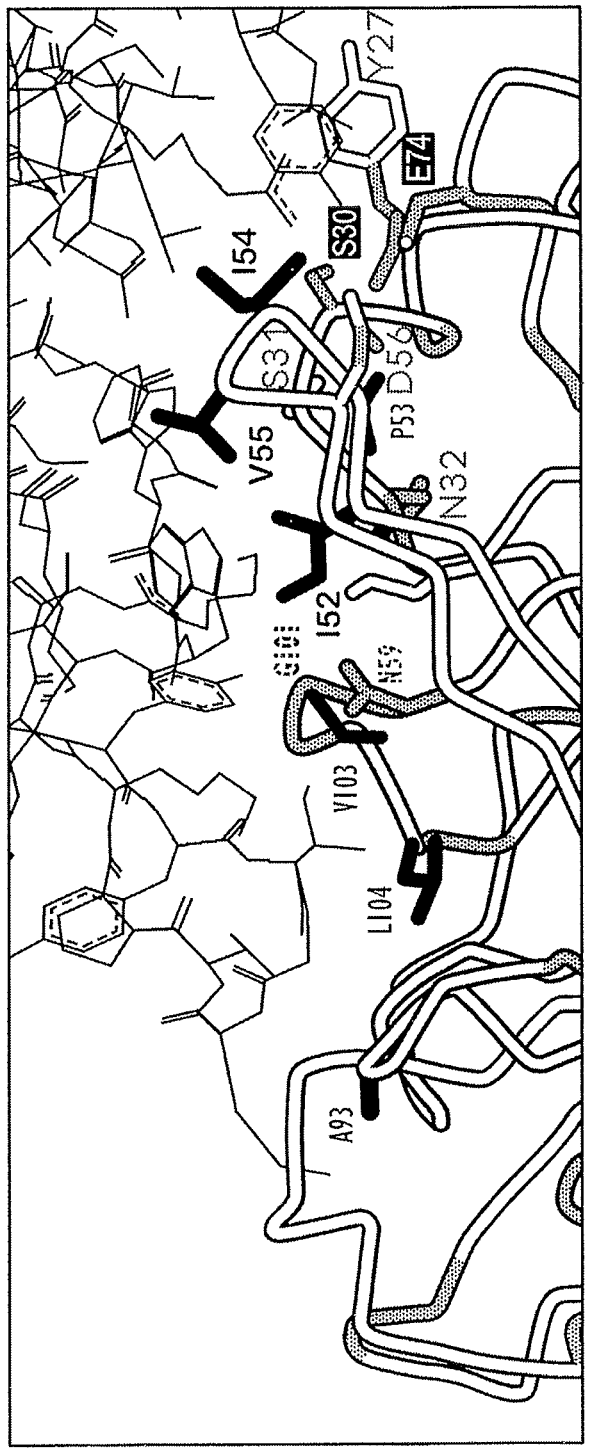
FIG. 5 depicts a portion of the co-crystal structure of GC1008(Fab) and human TGFβ. The heat map analysis of FIGS. 6A-6C is visualized with respect to residues Y27, S30, S31, N32, I52, P53, I54, V55, D56, N59, E74, G101, V103 and L104of the heavy chain (SEQ ID NO: 1) and residue A93 of the light chain (SEQ ID NO: 2).
Figure 6A:
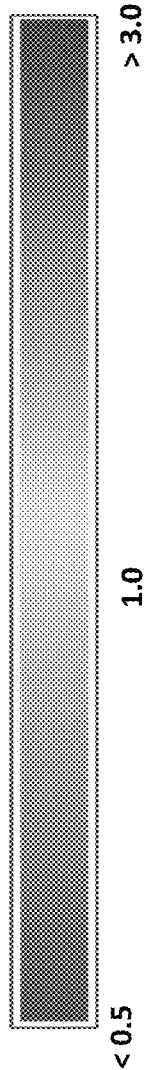
Figure 6B:
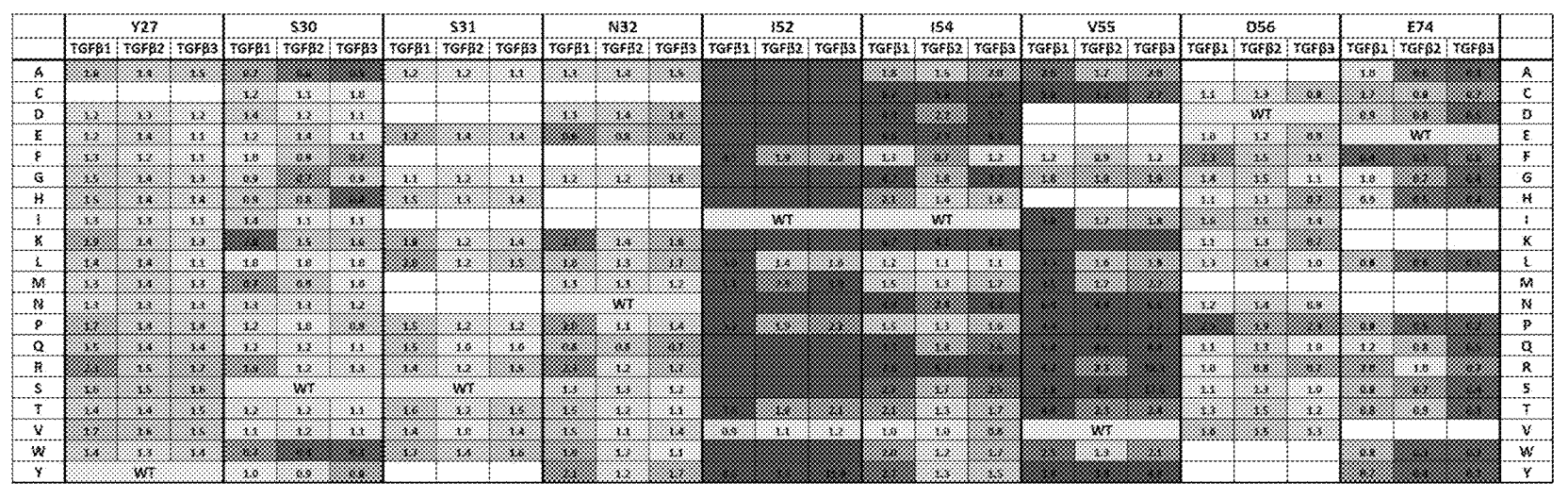

The heat ma analysis of FIGS. 6A-6C is visualized in FIG. 5, which shows the 3D structure of GC1008 bound to TGFβ. The gray chain represents GC1008, and the black chain represents TGFβ2. Residues I52, I54, and V55 are labeled black letters; residues Y27, S31, N32, and D56 are labeled in gray; and residues S30 and E74 are labeled in white according to the color scheme used for the heat ma analysis, shown at the bottom of FIG. 6A. That is, the black, gray, and white labels of FIG. 5 correspond to the red, yellow, and green colors of the color scheme of FIGS. 6A-C. An additional six residues labeled in smaller font, P53, N59, G101, V103. L104, and A93 (light chain), are similarly colored according to the heat ma analysis. Based on the mutagenesis analysis, the most sensitive positions (I52, I54, V55 in black letters) are paratope residues interacting with the core of the completely conserved TGFβhydrophobic patch region, whereas the most tolerant positions (S30, E74 in white letters) are further away and interact with the TGFβhelix three region.

What is claimed is:

1. An isolated human antibody or antigen-binding fragment thereof that binds to and neutralizes human TGFβ1, TGFβ2 and TGFβ3, comprising
   a heavy chain variable (VH) domain comprising SEQ ID NO:1 with a substitution selected from the group consisting of S30A, S30H, S30W, E74A, E74C, E74D, E74F, E74G, E74H, E74L, E74P, E74Q, E74R, E74S, E74T, E74W, and E74Y; and
   a light chain variable (VL) domain comprising SEQ ID NO:2.

2. The antibody of claim 1, wherein the VH domain further comprises a human IgG constant region.

3. The antibody of claim 2, wherein the IgG constant region is a human IgG4 constant region.

4. The antibody of claim 3, wherein the antibody further comprises a human κ constant region.

5. The antibody of claim 4, wherein the human IgG4 constant region comprises SEQ ID NO:3, and the human κ constant region comprises SEQ ID NO:4.

6. The antigen-binding fragment of claim 1, wherein the antigen-binding fragment comprises a Fab, Fab', F(ab')₂, scFv, or di-scFv.

7. A pharmaceutical composition comprising the antibody or antigen-binding fragment of claim 1.

8. A method of making the antibody or antigen-binding fragment of claim 1, comprising
   providing a host cell comprising nucleotide sequences encoding the heavy chain and light chain, respectively, of the antibody or antigen-binding fragment, and
   culturing the host cell under conditions that allow expression of the nucleotide sequences.

9. A method of treating a patient in need of inhibition of one or more of TGFβ1, β2 and β3, comprising administering to the patient the antibody or antigen-binding fragment of claim 1 or 5.

10. The method of claim 9, wherein the patient has a fibrotic disease, cancer, or an immune-mediated disease.

11. The method of claim 9, wherein the patient has renal insufficiency.

12. The method of claim 9, wherein the patient has focal segmental glomerulosclerosis.

13. The method of claim 9, wherein the patient has idiopathic pulmonary fibrosis.

14. The method of claim 9, wherein the patient has systemic sclerosis.

15. An isolated nucleic acid encoding the heavy chain, or both the heavy and light chains, of a human antibody or antigen-binding fragment thereof that binds to and neutralizes human TGFβ1, TGFβ2 and TGFβ3, wherein the antibody or fragment comprises
   a heavy chain variable (VH) domain comprising SEQ ID NO:1 with a substitution selected from the group consisting of S30A, S30H, S30W, E74A, E74C, E74D, E74F, E74G, E74H, E74L, E74P, E74Q, E74R, E74S, E74T, E74W, and E74Y; and
   a light chain variable (VL) domain comprising SEQ ID NO:2.

16. A vector comprising the isolated nucleic acid of claim 15.

17. A host cell comprising the vector of claim 16.

* * * * *